United States Patent
Kandula

(10) Patent No.: US 11,903,992 B2
(45) Date of Patent: Feb. 20, 2024

(54) COMPOSITION COMPRISING LIDOCAINE, L-CARNOSINE AND DEXPANTHENOL

(71) Applicant: Cellix Bio Private Limited, Hyderabad (IN)

(72) Inventor: Mahesh Kandula, Andhra Pradesh (IN)

(73) Assignee: Cellix Bio Private Limited, Hyderabad (IN)

( * ) Notice: Subject to any disclaimer, the term of this patent is extended or adjusted under 35 U.S.C. 154(b) by 0 days.

(21) Appl. No.: 17/650,664

(22) Filed: Feb. 10, 2022

(65) Prior Publication Data

US 2022/0233629 A1 Jul. 28, 2022

Related U.S. Application Data

(63) Continuation of application No. PCT/IB2022/050058, filed on Jan. 5, 2022.

(30) Foreign Application Priority Data

| Jan. 23, 2021 | (IN) | 202141003284 |
| Feb. 17, 2021 | (IN) | 202141006680 |
| Apr. 8, 2021 | (IN) | 202141016620 |
| Oct. 24, 2021 | (IN) | 202141048439 |

(51) Int. Cl.

| A61K 38/05 | (2006.01) |
| A61K 31/167 | (2006.01) |
| A61K 31/164 | (2006.01) |
| A61K 31/728 | (2006.01) |
| A61K 47/12 | (2006.01) |
| A61K 9/00 | (2006.01) |
| A61K 47/18 | (2017.01) |
| A61K 47/02 | (2006.01) |
| A61K 47/32 | (2006.01) |
| A61K 47/10 | (2017.01) |
| A61K 47/26 | (2006.01) |

(52) U.S. Cl.
CPC ............. *A61K 38/05* (2013.01); *A61K 9/006* (2013.01); *A61K 31/164* (2013.01); *A61K 31/167* (2013.01); *A61K 31/728* (2013.01); *A61K 47/02* (2013.01); *A61K 47/10* (2013.01); *A61K 47/12* (2013.01); *A61K 47/186* (2013.01); *A61K 47/26* (2013.01); *A61K 47/32* (2013.01)

(58) Field of Classification Search
None
See application file for complete search history.

(56) References Cited

U.S. PATENT DOCUMENTS

| 6,387,352 B1 * | 5/2002 | Johansen | A61K 8/24 |
| | | | 424/57 |
| 10,646,476 B2 * | 5/2020 | Rumio | A61P 1/00 |
| 2013/0039881 A1 * | 2/2013 | Conti | A61P 1/04 |
| | | | 514/57 |

FOREIGN PATENT DOCUMENTS

| CA | 2746087 A1 | | 1/2012 |
| CN | 1114944409 | * | 8/2020 |
| WO | 2010062153 A1 | | 6/2010 |

OTHER PUBLICATIONS

Shahid Beheshti University of Medical Sciences (ClinicalTrials.gov, Available online Mar. 21, 2011) (Year: 2011).*
Chapter 1 (Pharmaceutical solutions for oral administration, available Jul. 5, 2008). (Year: 2008).*
Melatonin Versus Ketorolac as an Adjuvant in Lidocaine Intravenous Regional Anesthesia.
Lidocaine: an inhibitor in the free-radical-induced hemolysis of erythrocytes.
Pfizer, Inc. v. Apotex, Inc., 480 F.3d 1348, 82 U.S.P.Q.2d 1321 (Fed. Cir. 2007).
Stephen M. Berge (Pharmaceutical Salts, J. Pharm. Sci., 66(1):1-19 (Jan. 1977) ("Berge").

* cited by examiner

*Primary Examiner* — Melissa S Mercier
(74) *Attorney, Agent, or Firm* — S. Elizabeth Miller, Esq.

(57) ABSTRACT

The present disclosure provides a composition comprising Lidocaine or salt or hydrate or solvate thereof, L-Carnosine or salt or hydrate or solvate thereof and dexpanthenol or salt or hydrate or solvate thereof. The composition may further comprise one or more other active agents. In an embodiment, the composition is formulated as an oral formulation. The compositions of the present disclosure may find utility in treatment of oral mucositis, ulcers, ulcer mediated pain and the like conditions. Aspects of the present disclosure also relates to method of treating oral, pharyngeal, oropharyngeal and esophageal diseases or conditions using the advantageous compositions of the present disclosure.

16 Claims, No Drawings

COMPOSITION COMPRISING LIDOCAINE, L-CARNOSINE AND DEXPANTHENOL

PRIORITY

The present application is a continuation of International Patent Application No. PCT/2022/050058, which was filed Jan. 5, 2022, which claims benefit of Indian provisional Application No. 202141003284 filed on Jan. 23, 2021, Indian provisional Application No. 202141006680 filed on Feb. 17, 2021, Indian provisional Application No. 202141016620 filed Apr. 8, 2021, and Indian provisional Application No. 202141048439 filed Oct. 24, 2021, the entire disclosures of which are relied on for all purposes and are incorporated into this application by reference.

FIELD OF THE INVENTION

The present disclosure generally relates to the field of compositions. In particular, the present disclosure provides an oral formulation comprising Lidocaine or salt or hydrate or solvate thereof, L-Carnosine or salt or hydrate or solvate thereof and dexpanthenol or salt or hydrate or solvate thereof. The compositions of the present disclosure may find utility in treatment of oral mucositis, oral ulcers, ulcer mediated pain and the like oral, pharyngeal, oropharyngeal and esophageal diseases/conditions.

BACKGROUND OF THE INVENTION

Oral health is recognized as an essential component of quality of life. The presence of oral diseases can affect a person's growth and development, as well as their psychic, productive and social capacity. Oral diseases are a highly prevalent group of pathologies in the world.

Inflammation is a biological response of the immune system that can be triggered by various infectious, immunological, physical, chemical, including chemotherapeutic drugs, biologic response modifiers, radiation therapy, and/or surgery. Inflammatory reactions include oral mucositis, oral stomatitis, oral ulcers and esophagitis are the inflammatory conditions of the mucous lining of the upper gastrointestinal tract from mouth to stomach. This reaction progress to oral pain, ulcers and infection, interfering with eating, talking, taste, chewing and swallowing and often lasting a few days.

Oral ulceration is a common condition characterized by the repeated formation of benign and non-contagious mouth ulcers in oral cavity and induce traumatic, infective, aphthous, ulceration related to dermatoses, drug-induced, ulceration as a manifestation of systemic disease, and ulceration due to malignancy. Oral ulcers are frequent lesions of the oral mucosa. Oral ulcers affect approximately 20% of the population, especially adolescents and young adults.

Esophagitis is a disease characterized by inflammation of esophageal mucosa. In some severe cases, untreated esophagitis can lead to alterations in the structure and function of the esophagus. Esophagitis etiologies include radiation, allergies, infections, dysmotility, local injury caused by medications, pill esophagitis and eosinophilic esophagitis (EoE), and it is a common toxicity of cancer treatment that can be caused by radiation therapy, characterized by disruption of the epithelium due to damage to the underlying basal cells.

Oral pain is a serious problem for many individuals, and it takes on a variety of guises. Pain must be appropriately managed to best ensure positive outcomes for patients with mucositis. Topical agents, growth factors, systemic analgesics and non-opioid strategies are used for oral pain. Local anesthetics are also used for the prevention of oral pain resulting from dental procedures.

Aphthous stomatitis is a painful and often persistent inflammatory process of the oral mucosa that can appear secondary to various well-characterized disease processes. Idiopathic recurrent aphthous stomatitis is described to as recurrent aphthous stomatitis. Local trauma, genetic factors, nutritional deficiencies, viral and bacterial infections, and immune or endocrine disturbances have all been implicated as etiological factors of frequent oral ulcerations.

Oral diseases associated pain is a self-limiting condition, currently there is no agent available to consistently prevent or treat this condition. The goal is to decrease the severity and duration of oral mucositis or oral inflammatory pain and to provide relief of discomfort, inflammation, and prevent or treat infection until recovery. There is a need for further compositions and methods that can be used to treat or prevent a wide variety of oral diseases.

The various lidocaine preparations, in the form of sprays or viscous solutions, are currently used for local anesthesia of the oral cavity and pharynx, but the effect is short lasting and the formulations are not very patient friendly because of unpleasant taste and texture. Such preparations are understood to be of limited, if any, effect in management of pain in patients with oral mucositis and do not assist in reducing the inflammation and improving healing process of stomatitis, mucositis and ulcers.

To solve the above problems, particularly, for treatment of oral, pharyngeal, oropharyngeal and esophageal diseases/conditions significant efforts have been put forth by the researchers. However, none of the existing approaches seem to satisfy the existing needs. A need is also felt of improved formulations that are easy to administer and helps in improving patient compliance. The present disclosure satisfies the existing needs, at least in part, and overcomes one or more disadvantages of the conventional approaches.

OBJECTS OF THE INVENTION

One of the objects of the present disclosure is to provide a composition that may overcome the limitations associated with the conventional compositions.

Another object of the present disclosure is to provide a composition that exhibits superior storage stability and functional reciprocity.

Further object of the present disclosure is to provide a composition that is easy to prepare and is economical.

Another object of the present disclosure is to provide a composition that affords healing of oral mucosal ulcers, reduces inflammation mediated pain and/or eosinophilia.

Yet another object of the present disclosure is to provide a composition that provides immediate relief from pain associated with oral, pharyngeal, oropharyngeal and esophageal disease/condition while also targeting, treating and/or providing palliative treatment for the underlying disease/condition.

Still another object of the present disclosure is to deliver the active agents either simultaneously or concurrently or concomitantly to a subject for treatment of the disease.

SUMMARY OF THE INVENTION

The present disclosure generally relates to the field of compositions. In particular, the present disclosure provides an oral formulation comprising Lidocaine or salt or hydrate or solvate thereof, L-Carnosine or salt or hydrate or solvate thereof and dexpanthenol or salt or hydrate or solvate thereof. The compositions of the present disclosure may find utility in treatment of oral mucositis, oral ulcers, ulcer mediated pain and the like oral, pharyngeal, oropharyngeal and esophageal diseases/conditions.

An aspect of the present disclosure provides a composition comprising: Lidocaine or salt or hydrate or solvate thereof, L-Carnosine or salt or hydrate or solvate thereof and dexpanthenol or salt or hydrate or solvate thereof, said composition being formulated as an oral formulation. In an embodiment, the composition is formulated as an oral rinse formulation.

The composition of the present disclosure comprises Lidocaine or salt or hydrate or solvate thereof, L-Carnosine or salt or hydrate or solvate thereof and dexpanthenol or salt or hydrate or solvate thereof in a weight ratio ranging from 1:1:1 to 7:1:20. In an embodiment, Lidocaine or salt or hydrate or solvate thereof, L-Carnosine or salt or hydrate or solvate thereof and dexpanthenol or salt or hydrate or solvate thereof are present in the composition in a weight ratio ranging from 1:1:1 to 5:1:10.

In an embodiment, the composition includes an excipient. The excipient is selected from any or a combination of: a diluent, an anti-oxidant, a preservative, a solvent, a flavoring agent, a sweetener, a fatty acid or derivative thereof, an amino acid or metabolite or derivative thereof, a surfactant, a solubilizer and a stabilizer.

In accordance with an embodiment of the present disclosure, the composition comprises: Lidocaine or salt or hydrate or solvate thereof in an amount ranging from 0.25% w/v to 10% w/v; L-Carnosine or salt or hydrate or solvate thereof in an amount ranging from 0.25% w/v to 5% w/v; dexpanthenol or salt or hydrate or solvate thereof in an amount ranging from 0.5% w/v to 25% w/v; a polyhydric alcohol in an amount ranging from 5% w/v to 30% w/v; an anti-oxidant in an amount ranging from 0.01% w/v to 3% w/v; a buffer in an amount ranging from 0.02% w/v to 5% w/v; a surfactant in an amount ranging from 1% w/v to 30% w/v; a sweetener in an amount ranging from 0.5% w/v to 25% w/v; a preservative in an amount ranging from 0.01% w/v to 5% w/v; and water in an amount ranging from 35% w/v to 90% w/v.

The polyhydric alcohol is selected from polyhydric alkanes, polyhydric alkane esters, polyalkene glycols, and mixtures thereof. The anti-oxidant is selected from sodium metabisulfite, vitamin A, tocopherol, ascorbic acid or salt or derivative thereof, tartaric acid or salt or derivative thereof, retinyl palmitate, sesamol, thiol derivatives, Butylated Hydroxy Anisole (BHA), Butylated Hydroxyl Toluene (BHT), and mixtures thereof. The buffer is selected from citric acid or salt or derivative thereof, benzoic acid or salt or derivative thereof, sorbic acid or salt or derivative thereof, succinic acid or salt or derivative thereof, and mixtures thereof. The sweetener is selected from sorbitol, xylitol, mannitol, maltitol, inositol, allitol, altriol, dulcitol, galactitol, glucitol, hexitol, iditol, pentitol, ribitol, erythritol, and mixtures thereof.

In some embodiments the composition may include one or more other active agents along with local anesthetic selected from the group of antimicrobial agents (include antibiotics, antiviral, antibacterial), JAK inhibitors, amino acids, corticosteroids, vitamins, immunosuppressant, NO (nitric oxide) releasing drugs, PDE inhibitors, anti-inflammatory agent, non-steroidal anti-inflammatory agents, anti-flatulent, hormones, and anti-ulcer.

In embodiment, the composition further includes hyaluronic acid or salt or derivative thereof in an amount ranging from 0.02% w/v to 15% w/v. In an embodiment, the composition has a pH ranging from 4.5 to 7.5.

DETAILED DESCRIPTION OF THE INVENTION

The present disclosure generally relates to the field of pharmaceutical compositions.

As used herein, the following terms and phrases shall have the meanings set forth below. Unless defined otherwise, all technical and scientific terms used herein have the same meaning as commonly understood to one of ordinary skill in the art. It is also understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "an active agent" or "an active ingredient" refers not only to a single active agent but also to a combination of two or more different active agents, "a dosage form" refers to a combination of dosage forms as well as to a single dosage form, and the like.

The term "active agent" or "therapeutic agent", encompass not only the specified molecular entity but also its pharmaceutically acceptable, pharmacologically active analogs, including, but not limited to, salts, esters, amides, prodrugs, conjugates, active metabolites, and other such derivatives, analogs, and related compounds.

The term "combination therapy" or "combined treatment" or "in combination" as used herein denotes any form of concurrent or concomitantly or co-administration of active agents for treating oral mucositis, ulcers, ulcer mediated pain and the like oral, pharyngeal, oropharyngeal and esophageal diseases/conditions.

The terms "treating" and "treatment" as used herein refers to reduction in severity and/or frequency of symptoms, elimination of symptoms and/or underlying cause, and improvement or remediation of damage caused thereby. Thus, "treating" a subject/patient as described herein encompasses treating oral, pharyngeal, oropharyngeal and esophageal diseases. The ulcers and the like conditions as disclosed herein includes oral ulcers that are chronic lesion or painful sores or seen on the lining of oral mucosa, plausibly accompanied by microbial infection(s). Oral mucositis is a painful inflammation and ulceration of the mucous membranes. Oral mucositis is a common and often debilitating complication of cancer treatment. HIV patients suffer from persistent, painful ulcers seen on the soft palate, buccal mucosa, tonsillar area or tongue, which are referred to as aphthous ulcers. Such conditions are more or less associated with painful sensation, either acute or chronic. The compositions of the present disclosure, although preferably, may be used for treatment of such painful oral, pharyngeal, oropharyngeal and esophageal conditions (such as radiation induced esophagitis), eosinophilic esophagitis the same may be used for other such conditions as well, wherein relieving pain in a subject and/or remediation/reversal of oxidative stress to prevent and/or cure the underlying disorder associated with heightened oxidative stress in a subject.

The composition of the present invention is useful in the treatment of radiation induced pain in mucositis, oral ulcers, aphthous ulcers and stomatitis patient. The irradiation-induced histological changes leading to oral mucositis, stomatitis and ulcers, together with salivary quantitative and qualitative changes, have been reported to facilitate yeast and pathogenic bacterial growth. Inflammation of the mucosa is a common, dose limiting complication of high dose chemotherapy and radiotherapy in cancer patients. Severe impairment of the patient's general condition is associated with subsequent bacterial superinfection. Long term hospitalization such cancer patients have substantial changes in oral microflora such microbial colonization within the oral cavity aggravation of the mucositis leading to severe clinical symptoms. Ulceration of the oral mucosa interrupts the natural defense barrier or mucosal layer and provides oral microorganisms and inflammatory cytokines to enter into underlying tissues and the systemic blood supply. 93% oral colonization and infection are frequently noted in the patients. The prevalent bacterial pathogens species in mucositis is *Scardovia* spp., *Lactobacillus* spp., *Streptococcus* spp., *Actinomyces* spp., *Staphylococcus* spp., *Enterococcus* spp., *Fusobacterium* spp., *Prevotella* sp., *Actinobacillus* spp., and *Candida* spp. and others are observed in the oral cavity of radiotherapy, radio chemotherapy treated patients.

Microbial infections are also very common in open wounds, cuts, surgical wound, burns rashes commonly found pathogens include *Staphylococcus aureus*, *Escherichia coli*, *Staphylococcus epidermidis*, *S. aureus*, *Pseudomonas aeruginosa*, *Klebsiella pneumonia*, *Proteus mirabilis*, *Proteus vulgaris*, *S. mutans*, *A. actinomycetemcomitans*, *P. gingivalis*, *F. nucleatum*, and *S. gordonii* and the fungal pathogens are *Candida albicans*, *Aspergillus fumigatus* and others.

The pathogenesis of mucositis is multifactorial and involves not only the epithelium, but also the cells and tissues within the submucosa Signaling from damaged endothelium, fibroblasts and infiltrating leukocyte cells contributes to apoptosis, loss of renewal, atrophy and ulceration.

The initiation of mucositis, stomatitis, ulcers are triggered by oxidative stress and the generation of reactive oxygen species (ROS), direct DNA and non-DNA damage, and activation of the innate immune response. These events follow the release of endogenous damage-associated molecular pattern molecules from injured cells of the basal epithelial layers, submucosa, and endothelium. Following initiation, ROS and the innate immune response further damage cell membranes, stimulate macrophages and activate several transcription factors of which nuclear factor NF-κB plays a prominent role. Once activated, NF-κB-mediated gene expression results in a surge of many pro-inflammatory cytokines such as tumor necrosis factor-α (TNF-α), interleukin (IL)-6 and IL-1β and cyclooxygenase-2 (COX-2).

The patients receiving chemo or radiation therapy have large increase in the bacterial load that the patient is least capable of dealing. Ulcer colonization also results in the release of bacterial cell wall products and cytokine production. During the ulcerative phase of mucositis, bacterial colonization occurs with gram-positive, gram-negative, opportunistic bacteria, fungi and anaerobic organisms. Cell wall products from bacteria can activate tissue macrophages, leading to more production of the proinflammatory cytokines TNF-alpha, IL-Ibeta, and IL-6.

The term "dosage form" denotes any form of a pharmaceutical composition that contains an amount of active agent sufficient to elicit a desired therapeutic response.

The term "controlled release" refers to a drug-containing formulation or fraction thereof in which release of the drug is not immediate. The term "controlled release" as used herein includes sustained release, non-immediate release and delayed release formulations.

The term "sustained release" (synonymous with "extended release") is used in its conventional sense to refer to a drug formulation that provides for gradual release of a drug over an extended period of time.

The term "pharmaceutically acceptable" means the material incorporated into a pharmaceutical composition that can be administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration.

"Pharmacologically active" (or simply "active") as in a pharmacologically active derivative or analog, refers to a derivative or analog having the same type of pharmacological activity as the parent compound and approximately equivalent in degree.

The present disclosure generally relates to the field of compositions. In particular, the present disclosure provides an oral formulation comprising lidocaine or salt or hydrate or solvate thereof, L-Carnosine or salt or hydrate or solvate thereof and dexpanthenol or salt or hydrate or solvate thereof. The compositions of the present disclosure may find utility in treatment of oral mucositis, oral ulcers, ulcer mediated pain and the like oral, pharyngeal, oropharyngeal and esophageal diseases/conditions.

The present disclosure is, in part, on the premise of observation of the inventors of the present disclosure that the compositions and formulations of the present disclosure can afford a unique treatment option for oral mucositis, oral ulcers, ulcer mediated pain and the like oral, pharyngeal, oropharyngeal and esophageal diseases/conditions, wherein Lidocaine being a local anesthetic affords relief from pain, while L-Carnosine and dexpanthenol affords antioxidant, oxygen free-radical scavenger, wound healing, improves hydration, prevents dryness and modulate immune response in many different ways. L-carnosine, is an anti-neoplastic agent, and also can suppress apoptosis of human neutrophils and increase the phagocytic activity of macrophages coupled to oxygen free-radicals production. Accordingly, the compositions of the present disclosure including lidocaine, L-Carnosine and dexpanthenol exhibit strong functional reciprocity and synergy.

An aspect of the present disclosure provides a composition comprising: lidocaine or salt or hydrate or solvate thereof, L-Carnosine or salt or hydrate or solvate thereof and dexpanthenol or salt or hydrate or solvate thereof, said composition being formulated as an oral formulation.

The composition of the present disclosure comprises lidocaine or salt or hydrate or solvate thereof, L-Carnosine or salt or hydrate or solvate thereof and dexpanthenol or salt or hydrate or solvate thereof in a weight ratio ranging from 1:1:1 to 7:1:20.

In an embodiment, lidocaine or salt or hydrate or solvate thereof, L-Carnosine or salt or hydrate or solvate thereof and dexpanthenol or salt or hydrate or solvate thereof are present in the composition in a weight ratio ranging from 1:1:1 to 5:1:10.

In an embodiment, lidocaine or salt or hydrate or solvate thereof, L-Carnosine or salt or hydrate or solvate thereof and dexpanthenol or salt or hydrate or solvate thereof are present in the composition in a weight ratio ranging from 1:1:1 to 3:1:7.

In an embodiment, lidocaine or salt or hydrate or solvate thereof, L-Carnosine or salt or hydrate or solvate thereof and dexpanthenol or salt or hydrate or solvate thereof are present in the composition in a weight ratio of 2:1:5.

In some embodiments, the composition of the present disclosure contains a local anesthetic producing analgesic effect, an endogenous hormone and an antioxidant, provitamin B5, dipeptide, anti-oxidant, micronutrient, antacids, ionic solution of salts, for the treatment of radiation induced oral mucositis in cancer patients. Wherein, the local anesthetic is the lidocaine, providing pain relief in patients with oral mucositis; the melatonin is the endogenous hormone and an antioxidant that, blunts NLRP3 inflammasome activation, inhibition of iNOS/i-mtNOS, COX-2, and pro-inflammatory cytokines such as IL-1β or TNF-α, inhibition of NF-κB-dependent innate immune pathway activation, increases the expression and activity of endogenous antioxidant enzymes like superoxide dismutase (SOD), manganese superoxide dismutase catalase, glutathione peroxidase (GPx), glutathione reductase (GRd) and γ-glutamyl-cysteine synthase; provitamin B5 such as dexpanthenol have anti-inflammatory effects and strengthen the physical and antimicrobial barrier in radiation-damaged skin; dipeptide and an anti-oxidant such as L-carnosine promotes wound healing, immune function; similarly, zinc is reported to have wound healing function in epithelial or connective tissues of various organs, and reduces oral mucositis. The higher ionic solution of calcium and magnesium salts in the composition permeates the oral mucosa and activates different signaling pathways, resulting in apoptosis modulation, downregulation of mediators of pain and inflammation, and activation of wound healing and epithelial proliferation. Present composition for oral mucositis, stomatitis, and canker sores, has the potential to improve efficacy in radiation induced oral mucositis and reduce the morphine consumption. In an embodiment, the composition includes an excipient. The excipient is selected from any or a combination of: a diluent, an anti-oxidant, a preservative, a solvent, a zinc salt, a flavoring agent, a sweetener, a fatty acid or derivative thereof, an amino acid or metabolite or derivative thereof, a vitamin, a surfactant, a solubilizer and a stabilizer.

In an embodiment, the composition further includes one or more active ingredients, said active ingredient being different from lidocaine or salt or hydrate or solvate thereof, L-Carnosine or salt or hydrate or solvate thereof and dexpanthenol or salt or hydrate or solvate thereof.

In an embodiment, the local anesthetic agents other than lidocaine can be used. The non-limiting examples of other local anesthetic agent include benzocaine, clonidine, bupivacaine, ropivacaine, mepivacaine, morphine, fentanyl, orthoform, levo-bupivacaine, bibucaine, prilocaine, acetaminophen, procaine, diphenhydramine, polaprezinc, benzydamine, pentoxifylline, ortetracaine, ketamine and combinations thereof. In certain embodiments, the compositions may include combination of local anesthetic agents.

In some embodiments, the composition may include one or more other active agents in combination with local anesthetic agent. The other active agents may be selected from the group of antimicrobial agents (include antibiotics, antiviral, antibacterial), JAK inhibitors, amino acids, corticosteroids, vitamins, immunosuppressant, NO (nitric oxide) releasing drugs, PDE inhibitors, anti-inflammatory agent, non-steroidal anti-inflammatory agents, anti-flatulent, hormones, and anti-ulcer agents.

In certain embodiments, the one or more active ingredients include misoprostol, amifostine, palifermin, chlorhexidine gluconate, dusquetide, melatonin, indraline, androstenetriol, actovegin, rebamipide, EC-18, brilacidin, validive, streptomycin, kanamycin, neomycin, gentamicin, betamethasone, betamethasone esters, clobetasol, clobetasol propionate, clobetasone, clocortolone, diclofenac salts, doxepin, benzydamine HCl, clocortolone esters, dexamethasone, dexamethasone esters, diflorasone, diflucortolone, diflucortolone valerate, fluclorolone, flumetasone, fluocortin, fluocortolone, fluocortolone esters, fluprednidene acetate, fluticasone, fluticasone furoate, fluticasone propionate, halometasone, meprednisone, mometasone, mometasone furoate, triamcinolone, ulobetasol (halobetasol), 2-mercaptoethane sodium sulphonate, thalidomide, lenalidomide, pomaldoamide, 2-Mercaptoethylguanidine, methylprednisolone, beclomethasone dipropionate, fluocinonide, clobetasol, betamethasone sodium phosphate, prednisolone, colchicine, pentoxifylline, azathioprine, thalidomide, dapsone, mycophenolate mofetil, adalimumab, vitamin B12, clofazimine, levamisole, hydrocortisone sodium succinate, montelukast, triamcinolone, sulodexide and combinations thereof.

In another embodiment composition may include one or more antimicrobial agents including antibiotics, antiviral, antibacterial agents. The non-limiting example include amphotericin B, benzoxonium chloride, chlorhexidine, chlortetracycline, clotrimazole, cetylpyridinium chloride, domiphen bromide, amoxicillin, cephalexin, ciprofloxacin, clindamycin, azithromycin, sulfamethoxazole, trimethoprim, clavulanate, levofloxacin, doxycycline, eugenol, hexetidine, hydrogen peroxide, mepartricin, metronidazole, miconazole, minocycline, natamycin, neomycin, oxyquinoline, polynoxylin, sodium perborate, tetracycline, tibezonium iodide, amlexanox, acetylsalicylic acid, becaplernin, benzydamine, epinephrine/adrenalone, fluocinonide, tetracycline, minocycline, chlorhexidine gluconate, triclosan and a combination thereof.

In another embodiment composition may include one or more corticosteroids. Non-limiting examples of corticosteroids include: amcinonide, alclometasone dipropionate, betamethasone dipropionate, betamethasone valerate, clocortolone pivalate, clobetasone, clobetasol propionate, desoximetasone, diflucortolone valerate, desonide, halobetasol, diflorasone, diflorasone diacetate, propionate, flurandrenolide, fluocinonide, fluocinolone acetonide, halcinonide, hydrocortisone acetate, hydrocortisone valerate, hydrocortisone butyrate, hydrocortisone probutate, mometasone furoate, mapracorat, hydrocortisone acetate, methylprednisolone, prednicarbate, prednisolone, pefcalitol, triamcinolone acetonide and combinations thereof.

In another embodiment composition may include one or more anti-inflammatory agents. The non-limiting examples of anti-inflammatory agents include methotrexate, ciclosporin, vitamin D analogues like calcipotriol and combinations thereof. Non-limiting examples of calcineurin inhibitors include tacrolimus, pimecrolimus, vitamin B3 or derivatives thereof and combinations thereof.

In another embodiment composition may include one or more non-steroidal anti-inflammatory agents. Non-limiting examples of non-steroidal anti-inflammatory agents include diclofenac, indomethacin, sulindac, mefenamic acid, piroxicam, ibuprofen, ketoprofen, naproxen, phenylbutazone, meloxicam, nimesulide, celecoxib, etoricoxib W13I-1001, MRX-6, valdecoxib and combinations thereof.

In another embodiment, compositions may include one or more immunosuppressant. The non-limiting examples include azathioprine, mycophenolic acid, cyclosporines, leflunomide, teriflunomide, ciclosporin, pimecrolimus, tacrolimus, voclosporin, lenalidomide, pomalidomide, thalidomide, apremilast, sirolimus, everolimus, ridaforolimus, temsirolimus, umirolimus, zotarolimus, baricitinib, blisibimod, nilotinib, filgotinib, tofacitinib, upadacitinib, abatacept, belatacept, etanercept, pegsunercept, amlexanox, afilbercept, alefacept, rilonacept and a combination thereof.

In another embodiment, compositions may include one or more NO (nitric oxide) releasing drugs. The non-limiting examples include glyceryl trinitrate, isosorbide dinitrate, isosorbide mononitrate, isoamyl nitrite and other derivatives and analogs with the NO releasing properties.

In another embodiment, compositions may include one or more Phosphodiesterase (PDE) inhibitors such as PDE 4 inhibitors, PDE 5 inhibitors and PDE 3 inhibitors. The non-limiting examples include PDE 4 inhibitors such as apremilast, arofylline, atizoram, benafentrine, catramilast, CC-1088, CDP-840, CGH-2466, cilomilast, cipamfylline, crisaborole, denbutylline, difamilast, drotaverine, etazolate, filaminast, glaucine, HT-0712, ICI-63197 indimilast, irsogladine, lavamilast, lirimilast, lotamilast, luteolin, mesembrenone, mesembrine, mesopram, oglemilast, piclamilast, pumafentrine, revamilast Ro 20-1724, roflumilast, rolipram, ronomilast, RPL-554, RS-25344, tetomilast, tofimilast, YM-976, zardaverine, ibudilast, roflumilast; PDE 3 Inhibitors such as adibendan, amrinone (inamrinone), anagrelide, benafentrine, bucladesine, carbazeran, cilostamide, cilostazol, enoximone, imazodan, KMUP-1, meribendan, milrinone, olprinone, parogrelil, pimobendan, pumafentrine, quazinone, RPL-554, siguazodan, trequinsin, vesnarinone, zardaverine; PDE 5 inhibitors such as acetildenafil, aildenafil, avanafil, beminafil, benzamidenafil, dasantafil, icariin, gisadenafil, homosildenafil, lodenafil, mirodenafil, MY-5445, nitrosoprodenafil, norcarbodenafil, SCH-51866, sildenafil, sulfoaildenafil, T-0156, tadalafil, udenafil, vardenafil and a combination thereof.

In another embodiment, compositions may include one or more JAK inhibitors. The non-limiting examples of JAK inhibitors include abrocitinib, baricitinib, filgotinib, momelotinib, oclacitinib, peficitinib, ruxolitinib, tofacitinib, tasocitinib, CP-690550, upadacitinib, atiprimod, AZD-1480, baricitinib, CHZ868, cucurbitacin I (elatericin B, JSI-124) CYT387 lestaurtinib, NSC-7908, NSC-33994, pacritinib, peficitinib, ruxolitinib, SD-1008, cercosporamide, decernotinib (VX-509), peficitinib, TCS-21311, WHI-P 15 ZM-39923, ZM-449829 and combination thereof.

In another embodiment, compositions may include one or more amino acids and vitamins. Non-limiting examples of amino acids include alanine, glycine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, pyrrolysine, and others. The non-limiting examples of vitamins include Vitamin A, Vitamin C, Vitamin D, Vitamin E, Vitamin K, Vitamin B1 (thiamine), Vitamin B2 (riboflavin), Vitamin B3 (niacin), Vitamin B6 (pyridoxine), Vitamin B12 (cyanocobalamin), Pantothenic acid (B5), pantothenic acid salt forms, calcium d-pantothenate, Biotin (B7), Folate (folic acid or B9) and their derivatives or combination thereof.

In certain embodiments, measures to reduce the risk and severity of oral mucositis include improved oral hygiene to eliminate the presence of any irritants to the oral mucosa; use of local anesthetic, use of systemic analgesics as tissue injury activates nociceptive receptors which increase pain. A combination of treatments, such as local rinses with anesthetic agents in the range of 0.1 mg-100 mg such as lidocaine, dicyclonine, ketamine, a topical morphine solution, sodium chloride, doxepin and/or use of systemic analgesics in the range of 0.1 mg-100 mg for easing acute oral mucositis pain. Frequent rinsing with oral rinse helps to keep the mucosa moist, reduces caking of secretions, and soothes inflamed/ulcerated mucosa.

An oral rinse solution can also can comprise anti-flatulent agent such as aluminum hydroxide, magnesium hydroxide, magnesium carbonate, simethicone and others. Simethicone is also an oral anti-foaming agent used in the oral rinse composition in the range of 0.01 gm-50 gm.

An rinse solution can also can comprise preservatives one or more agents such as Benzoates, Sorbates—including potassium sorbate, calcium sorbate and sodium sorbate, Propionates, Nitrites, Antioxidants that inhibit oxidation: Sulfites, including sodiutb sulfite, sodium bisulfite, sodium metabisulfite, potassium bisulfite and potassium metabisulfite, Vitamin E (tocopherol), Vitamin C (ascorbic acid), Butylated hydroxyanisole (BHA), Butylated hydroxytoluene (BHT)—the powder form of BHA, disodium, ethylenediaminetetraacetic acid (EDTA), polyphosphates, citric acid, BKC, SOC and others.

In one embodiment, the pharmaceutical compositions and formulations of the present disclosure comprises a fixed dose combination of lidocaine, D-panthenol, L-carnosine, zinc stearate, heavy magnesium oxide, BKC, sodium hyaluronic acid and calcium carbonate with other excipients for the treatment of oral mucositis, stomatitis, esophagitis or ulcers with enhanced pharmacological effects and better efficacy to obtain improved therapeutic outcomes as disclosed herein.

In another embodiment, the pharmaceutical compositions and formulations of the present disclosure comprises a fixed dose combination of lidocaine, melatonin, D-panthenol, L-carnosine, zinc stearate, heavy magnesium oxide and calcium carbonate with other excipients (composition 1) for the treatment of oral mucositis with additive pharmacology effect and better efficacy as disclosed herein. In some embodiments, the pharmaceutical composition 1 can be combined with one or more other active agents for better therapeutic efficacy, improved compliance, minimize frequent dosing as well as reduce side effects In another embodiment, the pharmaceutical compositions and formulations of the present disclosure comprises a fixed dose combination of lidocaine hydrochloride, L-carnosine, benzydamine, D-panthenol, citric acid anhydrous, tri sodium citrate dehydrate, xylitol powder 90, glycerol, propylene glycol, benzalkonium chloride, sodium metabisulfite, sodium hyaluronate, PVP K30 and water (composition 2) for the treatment of oral mucositis with additive pharmacology effect and better efficacy as disclosed herein. In some embodiment, the pharmaceutical composition 2 can be combined with one or more other active agents for better therapeutic efficacy, improved compliance, minimize frequent dosing as well as reduce side effects.

In another embodiment, the pharmaceutical compositions and formulations of the present disclosure comprises a fixed dose combination of lidocaine HCl, L-Carnosine, mometasone furoate, D-Panthenol or dexpanthenol, citric acid anhydrous, tri sodium citrate dehydrate, xylitol powder 90, Glycerol, Propylene glycol, Benzalkonium chloride, Sodium metabisulfite, Sodium hyaluronate, PVP K30 and Water (composition 3) for the treatment of oral mucositis, eosinophilic esophagitis with additive pharmacology effect and better efficacy as disclosed herein. In some embodiment, the pharmaceutical composition 3 can be combined with one or more other active agents for better therapeutic efficacy, improved compliance, minimize frequent dosing as well as reduce side effects.

In another embodiment, the pharmaceutical compositions and formulations of the present disclosure comprises a fixed dose combination of lidocaine HCl, L-Carnosine, mometasone furoate, D-Panthenol or dexpanthenol and other pharmaceutically acceptable excipients for the treatment of oral mucositis, eosinophilic esophagitis as disclosed herein. In some embodiment, the pharmaceutical can be combined with one or more other active agents and are formulated in oral tablet, lozenge, spray, aerosol, foam, gel, gum, chewable tablet, buccal tablet, oral films, effervescent tablet, oral dispersible powder with therapeutically effective amounts for the treatment of a particular oral disease or conditions.

Exemplified oral dosage form composition containing Lidocaine HCl, L-Carnosine, D-panthenol and mometasone and other pharmaceutically acceptable excipients:

| S. No | Ingredients | mg/tab |
|---|---|---|
| 1 | Mannitol | 400.96 |
| 2 | Cal D-Panthenol (D-Panthenol) | 21.54 |
| 3 | L-Carnosine | 10 |
| 4 | Heavy magnesium oxide | 25 |
| 5 | Calcium carbonate | 25 |
| 6 | CCS | 10 |
|   | Binder solution | |
| 7 | Hypromellose 5 cps | 10 |
| 8 | Simethicone 30% emulsion | 25 |
| 9 | Water | q.S |
|   | Extragranular | |
| 10 | Lidocaine | 100 |
| 11 | Mometasone | 1 |
| 12 | Aerosil | 6.5 |
| 13 | Zinc stearate | 6.5 |
| 14 | Peppermint flavor | 6.5 |
| 15 | Avg tablet weight | 648 |

In some embodiments, the pharmaceutical composition may further include any one or a combination other active agents selected from a group comprising corticosteroid, antimicrobial agents (antibiotic agents or antifungal agent or antiviral agents or anti-infective agents), immunosuppressant, anti-inflammatory agent, NO releasing drugs, JAK inhibitors and PDE inhibitors selected in a dosage form at therapeutically effective amounts for the treatment of a particular oral disease or conditions Further Embodiments Composition 1a: Composition 1 in combination with antimicrobial agents (antibiotic agents or antifungal agents or antiviral agents or anti-infective agents).

Composition 1b: Composition 1 in combination with corticosteroid.

Composition 1c: composition 1 in combination with immunosuppressant.

Composition 1d: composition 1 in combination with NO releasing drugs.

Composition 1e: composition 1 in combination with PDE inhibitors.

Composition 1f: composition 1 in combination with anti-inflammatory agents.

Composition 1fa: composition 1 in combination with JAK inhibitors.

In another embodiment, the composition 1 in the any of the above composition 1a to 1fa may be replaced with either composition 2 or composition 3.

Composition 1g: composition 1a in combination with immunosuppressant,

Composition 1h: composition 1a in combination with corticosteroid.

Composition 1i: composition 1a in combination with NO releasing drugs.

Composition 1j: composition 1a in combination with PDE inhibitors.

Composition 1k: composition 1a in combination with anti-inflammatory agents.

Composition 1ka: composition 1a in combination with JAK inhibitors.

Composition 1l: composition 1b in combination with NO releasing drugs.

Composition 1m: composition 1b in combination with PDE inhibitors.

Composition 1n: composition 1b in combination with anti-inflammatory agents.

Composition 1o: composition 1b in combination with antimicrobial agents.

Composition 1p: composition 1b in combination with immunosuppressant.

Composition 1pa: composition 1b in combination with JAK inhibitors.

In an embodiment, oral rinse composition comprises of lidocaine, melatonin, D-panthenol, L-carnosine, zinc stearate, heavy magnesium oxide and calcium carbonate with one or more antimicrobial agents and one or more other excipients In an embodiment, oral rinse composition comprises of lidocaine, melatonin, D-panthenol, L-carnosine, zinc stearate, heavy magnesium oxide and calcium carbonate with one or more corticosteroid and one or more other excipients In an embodiment, oral rinse composition comprises of lidocaine, melatonin, D-panthenol, L-carnosine, zinc stearate, heavy magnesium oxide and calcium carbonate with one or more immunosuppressant and one or more other excipients.

In an embodiment, oral rinse composition comprises of lidocaine, melatonin, D-panthenol, L-carnosine, zinc stearate, heavy magnesium oxide and calcium carbonate with one or more NO releasing drugs and one or more other excipients.

In an embodiment, oral rinse composition comprises of lidocaine, melatonin, D-panthenol, L-carnosine, zinc stearate, heavy magnesium oxide and calcium carbonate with one or more PDE inhibitors and one or more other excipients. Further PDE inhibitors can be selected from PDE 3 inhibitor, PDE 4 inhibitor and PDE 5 inhibitor.

In an embodiment, oral rinse composition comprises of lidocaine, melatonin, D-panthenol, L-carnosine, zinc stearate, heavy magnesium oxide and calcium carbonate with one or more anti-inflammatory agents and one or more other excipients.

In an embodiment, oral rinse composition comprises of lidocaine, melatonin, D-panthenol, L-carnosine, zinc stearate, heavy magnesium oxide and calcium carbonate with streptomycin and one or more other excipients.

In an embodiment, oral rinse composition comprises of lidocaine, melatonin, D-panthenol, L-carnosine, zinc stearate, heavy magnesium oxide and calcium carbonate with dexamethasone and one or more other excipients.

In an embodiment, oral rinse composition comprises of lidocaine, melatonin, D-panthenol, L-carnosine, zinc stearate, heavy magnesium oxide and calcium carbonate with rebamipide and one or more other excipients.

In an embodiment, oral rinse composition comprises of lidocaine, melatonin, D-panthenol, L-carnosine, zinc stearate, heavy magnesium oxide and calcium carbonate with amphotericin B and one or more other excipients.

In an embodiment, oral rinse composition comprises of lidocaine, melatonin, D-panthenol, L-carnosine, zinc stearate, heavy magnesium oxide and calcium carbonate with clotrimazole and one or more other excipients.

In an embodiment, oral rinse composition comprises of lidocaine, melatonin, D-panthenol, L-carnosine, zinc stearate, heavy magnesium oxide and calcium carbonate with azathioprine and one or more other excipients.

In an embodiment, oral rinse composition comprises of lidocaine, melatonin, D-panthenol, L-carnosine, zinc stearate, heavy magnesium oxide and calcium carbonate with pomalidomide and one or more other excipients.

In an embodiment, oral rinse composition comprises of lidocaine, melatonin, D-panthenol, L-carnosine, zinc stearate, heavy magnesium oxide and calcium carbonate with glyceryl trinitrate and one or more other excipients.

In an embodiment, oral rinse composition comprises of lidocaine, melatonin, D-panthenol, L-carnosine, zinc stearate, heavy magnesium oxide and calcium carbonate with isosorbide mononitrate and one or more other excipients.

In an embodiment, oral rinse composition comprises of lidocaine, melatonin, D-panthenol, L-carnosine, zinc stearate, heavy magnesium oxide and calcium carbonate with apremilast and one or more other excipients.

In an embodiment, oral rinse composition comprises of lidocaine, melatonin, D-panthenol, L-carnosine, zinc stearate, heavy magnesium oxide and calcium carbonate with amrinone and one or more other excipients.

In an embodiment, oral rinse composition comprises of lidocaine, melatonin, D-panthenol, L-carnosine, zinc stearate, heavy magnesium oxide and calcium carbonate with dasantafil and one or more other excipients.

In an embodiment, oral rinse composition 2 comprises of lidocaine, D-panthenol, L-carnosine, zinc stearate, heavy magnesium oxide and calcium carbonate with one or more antimicrobial agents at therapeutically effective amounts and one or more other excipients.

In an embodiment, oral rinse composition comprises of lidocaine, D-panthenol, L-carnosine, zinc stearate, heavy magnesium oxide and calcium carbonate with one or more corticosteroid at therapeutically effective amounts and one or more other excipients.

In an embodiment, oral rinse composition comprises of lidocaine, D-panthenol, L-carnosine, zinc stearate, heavy magnesium oxide and calcium carbonate with one or more immunosuppressant at therapeutically effective amounts and one or more other excipients.

In an embodiment, oral rinse composition comprises of lidocaine, D-panthenol, L-carnosine, zinc stearate, heavy magnesium oxide and calcium carbonate with one or more NO releasing drugs at therapeutically effective amounts and one or more other excipients.

In an embodiment, oral rinse composition comprises of lidocaine, D-panthenol, L-carnosine, zinc stearate, heavy magnesium oxide and calcium carbonate with one or more PDE inhibitors at therapeutically effective amounts and one or more other excipients. Further PDE inhibitors can be selected from PDE 3 inhibitor, PDE 4 inhibitor and PDE 5 inhibitor.

In an embodiment, oral rinse composition comprises of lidocaine, D-panthenol, L-carnosine, zinc stearate, heavy magnesium oxide and calcium carbonate with one or more anti-inflammatory agents at therapeutically effective amounts and one or more other excipients.

In an embodiment, oral rinse composition comprises of lidocaine, D-panthenol, L-carnosine, zinc stearate, heavy magnesium oxide and calcium carbonate with one or more other active agents as described in embodiments [0050], [0051], [0052], [0053], [0054], [0055], [0056], [0057], [0058], [0059], [0060] and [0061] at therapeutically effective amounts and one or more other excipients.

In an embodiment, oral rinse composition comprises of lidocaine, D-panthenol, L-carnosine, zinc stearate, heavy magnesium oxide and calcium carbonate with dexamethasone at therapeutically effective amounts and one or more other excipients.

In an embodiment, oral rinse composition comprises of lidocaine, D-panthenol, L-carnosine, zinc stearate, heavy magnesium oxide and calcium carbonate with diphenhydramine or doxepin at therapeutically effective amounts and one or more other excipients.

Non-limiting Example, Composition 2 with Benzydamine:

| Ingredients | % W/V |
| --- | --- |
| Lidocaine HCl | 2.0 |
| L-Carnosine | 1.0 |
| Benzydamine | 0.15 |
| D-Panthenol | 5.0 |
| Citric acid anhydrous | 0.1679 |
| Tri Sodium citrate dihydrate | 1.2135 |
| Xylitol powder 90 | 7.5 |
| Glycerol | 5.0 |
| Propylene glycol | 5.0 |
| Benzalkonium chloride | 0.02 |
| Sodium metabisulfite | 0.04 |
| Sodium hyaluronate | 0.2 |
| PVP K30 | 10.0 |
| Water | Qs to 100 |

Non-limiting Example, Composition 3 with a Corticosteroid:

| Ingredients | % W/V |
| --- | --- |
| Lidocaine HCl | 2.0 |
| L-Carnosine | 1.0 |
| Mometasone furoate | 0.05 |
| D-Panthenol | 5.0 |
| Citric acid anhydrous | 0.1679 |
| Tri Sodium citrate dihydrate | 1.2135 |
| Xylitol powder 90 | 7.5 |
| Glycerol | 5.0 |
| Propylene glycol | 5.0 |
| Benzalkonium chloride | 0.02 |
| Sodium metabisulfite | 0.04 |
| Sodium hyaluronate | 0.2 |
| PVP K30 | 10.0 |
| Water | Qs to 100 |

In an embodiment, oral rinse composition comprises of lidocaine, D-panthenol, L-carnosine, zinc stearate, heavy magnesium oxide and calcium carbonate with diphenhydramine and doxepin at therapeutically effective amounts and one or more other excipients.

In an embodiment, oral rinse composition comprises of lidocaine, D-panthenol, L-carnosine, zinc stearate, heavy magnesium oxide and calcium carbonate with benzydamine or/and doxepin at therapeutically effective amounts and one or more other excipients.

In an embodiment, oral rinse composition comprises of lidocaine, D-panthenol, L-carnosine, zinc stearate, heavy magnesium oxide and calcium carbonate with minocycline or/and doxycycline at therapeutically effective amounts and one or more other excipients.

In an embodiment, oral rinse composition comprises of lidocaine, D-panthenol, L-carnosine, zinc stearate, heavy magnesium oxide and calcium carbonate with benzydamine or/and doxepin or/and diphenhydramine at therapeutically effective amounts and one or more other excipients.

In an embodiment, oral rinse composition comprises of lidocaine, D-panthenol, L-carnosine, zinc stearate, heavy magnesium oxide and calcium carbonate with clotrimazole or miconazole at therapeutically effective amounts and one or more other excipients.

In an embodiment, oral rinse composition comprises of lidocaine, D-panthenol, L-carnosine, zinc stearate, heavy magnesium oxide and calcium carbonate with azathioprine at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with thalidomide or lenalidomide or pomalidomide at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with glyceryl trinitrate at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with isosorbide mononitrate at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with apremilast at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with amrinone at therapeutically effective amounts and one or more other excipients.

In an embodiment, oral rinse composition comprises of lidocaine, benzalkonium chloride, sodium metabisulfite, sodium hyaluronate, D-panthenol, L-carnosine, zinc stearate, heavy magnesium oxide and calcium carbonate with dasantafil at therapeutically effective amounts and one or more other excipients.

In another embodiment, the oral rinse solution may also include one or more local anti-infective agents in the range of 0.5 mg to 160 mg, such as aminoacridine hydrochloride, natamycin, pimaricin, polypasdone, getroxel and likes for decontamination of the oral cavity. The composition can further include anti-histamines and/or anti-inflammatory agents (non-steroidal and steroidal) in the range of 0.01 mg-150 mg such as hydrocortisone, glutamine, benzydamine, diphenhydramine, chlorpheniramine, prostaglandin E2, misoprostol, betamethasone, prednisone, indomethacin, histamine, colchicine and the likes. The oral rinse solution can include one or more antimicrobial (antibacterial and/or antifungal and/or antiviral) agents in the range of 1 µg-20 gm to clear the oral microflora. Examples of antimicrobial agents include polymixin E, tetracycline, tobramycin, amphotericin B, acyclovir, clotrimazole, methylparaben, propylparaben and the likes.

In another embodiment, the oral rinse composition can includes one or more anti-ulcer agents or agents which acts as mucosal barriers and coating agents in the range of 0.5-20 gm. These agents can bind to ulcers and mucosal surface acting as a barrier to irritants and promoting healing examples include sodium alginate, kaolin-pectin, magnesium hydroxide, and hydroxypropyl cellulose, sucralfate and the likes.

In another embodiment, the oral rinse composition can include one or more cytoprotectants such as Beta-carotene, azelastine hydrochloride, prostaglandins E1 and E2, dinoprostone, amifostine, vitamin E, xanthine derivatives and oxpentifylline.

In some embodiments, the oral rinse composition can include one or more hormones such as melatonin. Melatonin is also known as a potent anti-oxidant and/or a radioprotective agent. Melatonin is effective in preventing damage caused by oxidative stress. It reduces radiation-induced DNA damage and lipid peroxidation thus protecting the mucosal layer.

In some embodiment the oral rinse composition can include gabapentin for the treatment of pain related to radiation induced mucositis. The concentration of Gabapentin can be in the range of 100 mg to 3600 mg.

In some embodiments, the oral rinse composition can include mometasone or a pharmaceutically salt form for the treatment of eosinophilic esophagitis. The concentration of mometasone can be in the range of 0.01 mg to 40 mg.

In some embodiment the oral rinse composition can be used for oral mucositis and has the potential to improved efficacy in radiation induced oral mucositis; and to reduce the morphine consumption in the management of oral mucositis.

The composition may be formulated as a solid, semi-solid or liquid dosage form. Non-limiting examples of dosage forms includes tablet, lozenge, film (orally dissolvable or otherwise), capsule, caplet, modified release tablet or lozenge, suspension, solution, emulsion, granules, pellets, beads, powder, aerosol sprays cream, ointment, lotion, patches, gel, tablet in tablet, bilayer tablet, trilayer tablet, inlay tablet, capsule in capsule, tablet(s) in capsule, granules and/or pellets in capsule, pellets and tablet in capsules and the likes.

In an embodiment, the composition is formulated as an oral rinse formulation. It could also be noted during development of the formulation that L-Carnosine tends to increase the pH of the composition to about 8.5, which tend to increase the degradation of lidocaine. Further, it could be noted that L-Carnosine, being sensitive to oxygen tend to degrade, while Dexpanthenol requires neutral pH for stability. During the experimentation, it could be noted that presence of a buffer (e.g. a citrate buffer) and an anti-oxidant (e.g. sodium metabisulfite) in the composition, while maintaining pH of the resultant composition/formulation around 6.5±1 (i.e. ranging from about 5.5 to about 7.5), preferably at 6.5±0.5 and more preferably, at 6.5±0.2 affords dramatic improvement in the shelf life of the composition/formulation.

Accordingly, in accordance with an embodiment of the present disclosure, the composition includes: Lidocaine or salt or hydrate or solvate thereof in an amount ranging from 0.25% w/v to 10% w/v; L-Carnosine or salt or hydrate or solvate thereof in an amount ranging from 0.25% w/v to 5% w/v; dexpanthenol or salt or hydrate or solvate thereof in an amount ranging from 0.5% w/v to 25% w/v; a polyhydric alcohol in an amount ranging from 5% w/v to 30% w/v; an anti-oxidant in an amount ranging from 0.01% w/v to 3% w/v; a buffer in an amount ranging from 0.02% w/v to 5% w/v; a surfactant in an amount ranging from 1% w/v to 30% w/v; a sweetener in an amount ranging from 0.5% w/v to 25% w/v; a preservative in an amount ranging from 0.01% w/v to 5% w/v; and water in an amount ranging from 35% w/v to 90% w/v.

Examples of polyhydric alcohols useful in the compositions of the present disclosure include polyhydric alkanes, polyhydric alkane esters, polyalkene glycols, and mixtures thereof. Polyhydric alkanes can be propylene glycol, glycerin, glycerol, butylene glycol, hexylene glycol, 1,3-propanediol and the likes, but not limited thereto. Polyhydric alkane esters can be dipropylene glycol, ethoxydiglycol and the likes, but not limited thereto. Polyalkene glycols can be polyethylene glycol, polypropylene glycol and the likes, but not limited thereto. The compositions of the present disclosure include polyhydric alcohol in an amount ranging from 5% w/v to 30% w/v, preferably, in an amount ranging from 5% w/v to 25% w/v, and more preferably, in an amount ranging from 5% w/v to 20% w/v.

Examples of anti-oxidants useful in the compositions of the present disclosure include sodium metabisulfite, vitamin A, tocopherol, ascorbic acid or salt or derivative thereof, tartaric acid or salt or derivative thereof, retinyl palmitate, sesamol, thiol derivatives, Butylated Hydroxy Anisole (BHA), Butylated Hydroxyl Toluene (BHT), and mixtures thereof. However, any other anti-oxidant(s), as known to or appreciated by a person skilled in the art can also be used to serve its/their intended purpose as laid down in embodiments of the present disclosure.

Examples of buffers useful in the compositions of the present disclosure include citric acid or salt or derivative thereof, benzoic acid or salt or derivative thereof, sorbic acid or salt or derivative thereof, succinic acid or salt or derivative thereof, a bicarbonate salt of alkali earth metal, amino acids, an acid salt of an amino acid, an alkali salt of an amino acid and mixtures thereof. However, any other buffer(s), as known to or appreciated by a person skilled in the art can also be used to serve its/their intended purpose as laid down in embodiments of the present disclosure. In an embodiment, the buffer is citric acid or salt or derivative thereof. In an embodiment, the composition includes a combination of citric acid and trisodium citrate dihydrate as a buffer.

Examples of sweeteners useful in the compositions of the present disclosure include mannitol, sorbitol, polyethylene glycol (PEG) 6000 and 8000, Emdex, Nu-tab, Sweetrex, Mola-tab, Honey-tab, Sugar tab, non-sugar sweetening agents such as aspartame, sorbitol, xylitol, isomalt, saccharin, sodium saccharin, calcium saccharin, sucralose, acesulfame-K, steviol, steviosin, mannitol, erythritol, lactitol, and sugar sweetening agents such as sucrose, fructose, dextrose and mixtures thereof. However, any other natural or artificial sweetener can also be used in the compositions of the present disclosure. In an embodiment, the composition includes xylitol as a sweetener.

Examples of surfactants useful in the compositions of the present disclosure include anionic surfactants, nonionic surfactants, amphoteric surfactants and mixtures thereof. Anionic surfactants useful herein include, but are not limited to, sarcosine type surfactants or sarcosinates; taurates such as sodium methyl cocoyl taurate; alkyl sulfates such as sodium trideceth sulfate or sodium lauryl sulfate; sodium lauryl sulfoacetate; sodium lauroyl isethionate; sodium laureth carboxylate; sodium dodecyl benzenesulfonate and mixtures thereof. Nonionic surfactants that can be used in the compositions of the present disclosure include, but are not limited to, Polyvinylpyrrolidone (PVP), such as PVP K30, compounds produced by the condensation of alkylene oxide groups with an organic hydrophobic compound which may be aliphatic or alkyl-aromatic in nature. Examples of suitable nonionic surfactants include, but are not limited to, alkyl polyglucosides; block copolymers such as ethylene oxide and propylene oxide copolymers e.g. Poloxamers; ethoxylated hydrogenated castor oils; Alkyl polyethylene oxide e.g. Polysorbates, and/or; fatty alcohol ethoxylates; polyethylene oxide condensates of alkyl phenols; products derived from the condensation of ethylene oxide with the reaction product of propylene oxide and ethylene diamine; ethylene oxide condensates of aliphatic alcohols; long chain tertiary amine oxides; long chain tertiary phosphine oxides; long chain dialkyl sulfoxides; and mixtures thereof. The amphoteric surfactants useful in the compositions of the present disclosure include, but are not limited to, derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Examples of suitable amphoteric surfactants include, but are not limited to alkylimino-diprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolines, alkyl betaines, alkylamido betaines, alkylamidopropyl betaines, alkyl sultaines, alkylamido sultaines, and mixtures thereof. In certain embodiments, the amphoteric surfactant is selected from the group consisting of alkylamidopropyl betaines, amphoacetates such as sodium lauroamphoacetate and mixtures thereof. Mixtures of any of the above mentioned surfactants can also be employed.

In an embodiment, the composition includes a preservative in an amount ranging from 0.01% w/v to 3% w/v, preferably, ranging from 0.01% w/v to 2% w/v, more preferably, ranging from 0.01% w/v to 1% w/v and most preferably, ranging from 0.01% w/v to 0.5% w/v. Examples of preservatives useful in the compositions of the present disclosure include methyl paraben, propyl paraben, p-hydroxybenzoic acid esters, quaternary ammonium compounds such as benzalkonium chloride, sodium benzoate, benzyl alcohol, butanol, ethanol, isopropyl alcohol and the likes.

In an embodiment, the amino acids or metabolites or derivatives thereof include(s), but not limited to, glycine, glutamine, asparagine, arginine, lysine in biologically active enantiomeric forms, N-acetyl-cysteine, L-proline, L-leucine, lysine hydrochloride, L-methionine, L-phenylalanine, L-Threonine, T-thyrptophan, L-valine, L-histidine, L-aspartic acid, L-carnitine, choline, betaine, taurine, glycosaminoglycans including hyaluronic acid, chondroitin sulfate, glucosamine, L-glucosamine, heparins and mixtures thereof. In an embodiment, the composition includes hyaluronic acid or salt or derivative thereof in an amount ranging from 0.02% w/v to 15% w/v, preferably, ranging from 0.05% w/v to 2% w/v, more preferably, ranging from 0.1% w/v to 1% w/v and most preferably, ranging from 0.1% w/v to 0.5% w/v. In an embodiment, the composition includes sodium hyaluronate in an amount ranging from 0.02% w/v to 15% w/v, preferably, ranging from 0.05% w/v to 2% w/v, more preferably, ranging from 0.1% w/v to 1% w/v and most preferably, ranging from 0.1% w/v to 0.5% w/v.

Examples of stabilizers useful in the compositions of the present disclosure include, but not limited to, gums, agar and taste masking agents like acrylic polymers, copolymers of acrylates, celluloses, resins and mixtures thereof.

Examples of flavoring agents useful in the compositions of the present disclosure include, but not limited to, cherry, maple, pineapple, orange, raspberry, banana-vanilla, peppermint, butterscotch, strawberry, vanilla, apricot, cinnamon, honey, lime, peach-orange, peach-rum, raspberry, wild cherry, mint and mixtures thereof.

In an embodiment, the composition further includes zinc salts. Examples of zinc salts useful in the compositions of the present disclosure include, but not limited to, zinc oxide, zinc stearate, zinc L-carnosine, zinc acetate, zinc chloride, zinc bromide, zinc fluoride, zinc hexafluorosilicate, zinc iodide, zinc molybdate, zinc nitrate, zinc molybdite, zinc oxalate, zinc perchlorate, zinc tetrafluoroborate, zinc sulfate and mixtures thereof.

In an embodiment, the fatty acid(s) or derivatives thereof include(s), but not limited to, fatty acids with C1 to C30 carbons, which includes long chain fatty acids; saturated or unsaturated fatty acids and derivatives thereof (monounsaturated fatty acids (MUFAs) C18:1n-12c, C16:1n-5, C16:4n-1 and the polyunsaturated fatty acids (PUFAs) C16:3n-4, C20:3n-3, C20:4n-6, C21:5n-3 and C18:2n-9c,12t); hydrogenated fatty acids; fatty acid glycerides; polyoxyethylated oleic glycerides; monoglycerides and diglycerides; mono-, bi- or tri-substituted glycerides; glycerol mono-oleate esters; glycerol mono-caprate; glyceryl monocaprylate; dicaprylate; laurate, monolaurate; glyceryl palmitostearate; glyceryl behenate; diethyleneglycol palmitostearate; polyethyleneglycol stearate; polyoxyethyleneglycol palmitostearate; glyceryl mono palmitostearate; cetyl palmitate; polyethyleneglycol palmitostearate; dimethylpolysiloxane; mono- or di-glyceryl behenate; fatty acid derivatives such as diglyceryl lauryl fumarate (DGLF), diglyceryl lauryl succinate, diglyceryl capryl succinate, diglyceryl capryl fumarate; fatty alcohols associated with polyethoxylate fatty alcohols; cetyl alcohol; octyldodecanol; myristyl alcohol; isopropyl myristate, isopropyl palmitate, stearic acid, lauric acid, EPA, DHA, linoleic acid, linolenic acid, stearyl alcohol and mixture thereof. In an embodiment, the fatty acid derivatives includes any or a combination of: diglyceryl lauryl fumarate (DGLF), diglyceryl lauryl succinate, diglyceryl capryl succinate, and diglyceryl capryl fumarate.

Examples of other agents that can be included as part of the compositions of the present disclosure include a-Lipoic acid, cysteamine, folic acid, hydrolytic enzyme, mucotrol, polaprezinc, traumeel, tretinoin, vitamins (calcipotriene, calcitriol, ergosterol, 1α-hydroxycholecalciferol, vitamin D2, vitamin D3, ascorbic acid, calcium ascorbate, nicotinamide ascorbate, sodium ascorbate, α-carotene, β-carotene, δ-carotene, vitamin A, cobamamide, folic acid, hydroxocobalamin, sodium folate, vitamin B12, menadiol, menadione, menadoxime, menaquinones, phylloquinone, vitamin K5, inositol, atocopherol, γ-tocopherol, γ-tocopherol, vitamin E and or any combinations thereof.) mineral and their salts (such as zinc, selenium, potassium, copper, manganese, copper, aluminum, zinc sulfate, magnesium, magnesium aluminum hydroxide, magnesium sulfate, calcium phosphate, magnesium stearate, magnesium silicate, magnesium sulphate, magnesium chloride, magnesium bromide, magnesium acetate, magnesium lactate, magnesium pidolate, magnesium thiosulphate, magnesium sulphate, $Cu^{3+}$ salts such as copper sulfate pentahydrate, copper sulfate, copper malonate, copper citrate, copper oxalate, copper tartarate, copper lactate, copper chloride, copper bromide, copper pidolate, copper phosphate, copper nitrate, copper thiosulphate, $Al^{+3}$ salts such as aluminium oxide, aluminium palmitate, aluminum stearate, aluminum chloride, aluminum oxychloride, aluminum barium silicate, Aluminum magnesium hydroxide stearate, aluminum propionate aluminum dipropionate, aluminum aceto propionate, aluminum citro propionate, aluminum lacto propionate, aluminum tartaro propionate, aluminum acetodipropionate, aluminum citrodipropionate, aluminum lacto dipropionate, and aluminum tartarodipropionate and the likes, Polymers such as carbomer, methyl cellulose, sodium carboxyl methyl cellulose, carrageenan, colloidal silicon dioxide, hydroxypropyl cellulose, hydroxypropyl methyl cellulose, polyethylene oxide, hyaluroinic acid, hydrated silica, hydroxypropyl chitosan, chitosan sulfate, ethyl cellulose, hydroxypropyl cellulose, hydroxymethyl cellulose, carboxy methyl cellulose, polyethylene oxide, and chitosan pyrrolidone carboxylate and the likes.

While one or more embodiments of the present disclosure enumerates and describes a list of excipients that may be used in the composition to serve an intended purpose, it should be appreciated that one or more excipient may also serve more than one function, obviating the need of inclusion of separate excipient for the specified purpose. For example, citric acid or salt or derivative thereof when used as part of the composition while serving the need of a buffer, may also serve as a preservative and/or as an antioxidant, and consequently, it would be apparent to a skilled artisan that one may, in such a case, obviate use of preservative and/or antioxidant altogether or can adjust the amount(s) thereof. Although several embodiments of the present disclosure names few of the commonly used excipients, any other excipient known to or appreciated by a skilled person can also be used to realize the advantageous compositions of the present disclosure. Examples of useful excipients which can optionally be added to the composition are described in the Handbook of Pharmaceutical Excipients, 3rd edition, Edited by A. H. Kibbe, Published by: American Pharmaceutical Association, Washington DC, ISBN: 0-917330-96-X, and in Handbook of Pharmaceutical Excipients (4th edition), Edited by Raymond C Rowe—Publisher: Science and Practice.

In an embodiment, the composition is formulated as an oral rinse. The oral rinse formulation can be prepared by the method that includes: (a) preparing a first premix by taking a part of water (e.g. 2-50% of the total amount of water required in the formulation) in a compounding vessel and mixing D-Panthenol or salt or hydrate or solvate thereof therewith; (b) preparing a second premix by taking a part of water (e.g. 10-70% of the total amount of water required in the formulation) in a separate compounding vessel and mixing Lidocaine or salt or hydrate or solvate thereof, L-Carnosine or salt or hydrate or solvate thereof, a polyhydric alcohol, a buffer, an anti-oxidant, a surfactant, a sweetener and any other excipient therewith; (c) mixing the first premix with the second premix, preferably, while stirring the mixture; and (d) adjusting the final volume with remainder of the water to prepare the composition.

In an embodiment, the composition is formulated as an oral rinse. The oral rinse formulation that include hyaluronic acid or salt or derivative thereof can be prepared by the method that includes: (a) preparing a first premix by taking a part of water (e.g. 2-50% of the total amount of water required in the formulation) in a compounding vessel and mixing D-Panthenol or salt or hydrate or solvate thereof therewith; (b) preparing a second premix by taking a part of water (e.g. 10-70% of the total amount of water required in the formulation) in a compounding vessel and mixing Lidocaine or salt or hydrate or solvate thereof, L-Carnosine or salt or hydrate or solvate thereof, a polyhydric alcohol, a buffer, an anti-oxidant, a surfactant, a sweetener and any other excipient therewith; (c) preparing a third premix by taking a part of water (e.g. 5-40% of the total amount of water required in the formulation) in a compounding vessel and mixing hyaluronic acid or salt or derivative thereof therewith while stirring to obtain a clear viscous solution; (d) mixing the first premix with the second premix, preferably, while stirring the mixture; (e) mixing the third premix with the mixture (mixture of first and second premix) while stirring; and (f) adjusting the final volume with the remainder of the water to prepare the formulation.

In an embodiment, the composition is formulated into a chewy or hard or caramel based lozenge, pastilles, troches, soft lozenge, center or liquid filled lozenge, power-based lozenge, compressed lozenge, syrup-based lozenge, granulated lozenge, buccal and sublingual tablets. The lozenge formulation of the present disclosure may increase bioavailability and affords immediate relief from pain. Lozenge dosage forms are easy to administer for geriatric and pediatric patients who can't swallow tablets formulation. This formulation may help to keep the drug in contact to the oral cavity for longer time. The lozenge may be formulated as a modified release formulation (modified release can be controlled release, immediate release, phased release, timed release, sustained release, delayed release or a combination of immediate or quick or fast and sustained or slow or extended release). The lozenge can be formulated as a bi-layer, tri-layer tablet or multi-layer tablet to facilitate the delivery of at least two or more active agents. Typically, the carrier material for lozenge preparation includes sugar such as sucrose, dextrose, etc. Recently consumers have become concerned about the excessive levels of sugar contained within their diets. This concern has caused a demand for sugar-free products, including sugar-free medications. Pharmaceutical manufacturers have attempted to find alternative carrier bases in order to provide sugar-free lozenges. One such alternative carrier is a polyhydric alcohol such as xylitol. Polyhydric alcohols are considered as a viable alternative because they provide a sweet taste will mask the bitter taste of many medicinal agents. Lozenges made from polyhydric alcohols do suffer from one serious disadvantage. They dissolve very rapidly when placed in the oral cavity. For example, a lozenge made from a xylitol based carrier will dissolve completely within approximately 3 minutes of administration. Other polyhydric alcohols such as sorbitol or mannitol will also dissolve within 3 minutes of administration.

In an embodiment, non-limiting examples of excipients for preparing a compressed powder lozenge or compressed granulated lozenge, cast lozenge includes at least one diluents, at least one fillers, at least one glidants, at least one lubricants, at least one binders, at least one preservatives, at least one artificial or natural sweeteners or and at least one aroma or flavoring compounds. The lozenge may be formulated as a modified release formulation (modified can be controlled release, immediate release, phased release, timed release, sustained release, delayed release or a combination of immediate or quick or fast and sustained or slow or release). The lozenge can be formulated as a bi-layer, tri-layer tablet or multi-layer tablet to facilitate the delivery of at least two or more active agents.

In some embodiments, the compositions are formulated as cast lozenges comprising at least one base selected from fructo-oligosaccharides, crystalline sugar, candy base, isomalt or stevia; at least one aromas selected from natural aroma, essential oils such as citrus, mint oils, terpenes and sesquiterpenes, organic acids, alcohols, aldehydes, liquorice powder, menthol, peppermint oil or any fruit flavors; at least one taste enhancing ingredient such as saccharose, glutamic acid, E621 monosodium glutamate, MSG, E622 monopotassium glutamate, E623 calcium diglutamate, E625 Magnesium diglutamate); guanylic acid (a ribonucleotide) and its salts (E626 guanylic acid, E627 disodium guanylate, sodium guanylate, E628 dipotassium guanylate, E629 calcium guanylate); E630 inosinic acid, E631 disodium inosinate, E632 dipotassium inosinate, E633 calcium inosinate), E634 calcium 5'-ribonucleotides, E635 disodium 5'-ribonucleotides; E636 maltol, E637 ethyl maltol, E640 glycine and E641 L-leucine.

In certain embodiments, the present composition comprising local anesthetics with other agents not only reduces the pain but also reduces manifestation of oral candidiasis and other microbial infections. The instant invention provides mucosal protective effects, soothes oral lesions, reduces oral dryness, and counteracts radiation induced metabolic deficiencies. The composition also acts as detoxifying agent that removes ROS and also provides radio protective effects against radiation induced oral mucositis. The anti-oxidative effect significantly reduces the incidence of severe mucositis and ulcers and alleviate the pain sensation and mechanical sensitivity associated with oral mucositis and ulcers.

In the mucositis patients' irradiation-induced DNA damage interferes with the proliferation and differentiation of basal keratinocytes. The composition of present invention stimulates epithelization, granulation and restores epidermal layer completely after irradiation, it protects against mucositis by providing anti-oxidative and anti-inflammatory effects and by strengthening the physical and antimicrobial barrier function. Thus, the composition mitigates the negative effects of chemo and radiation therapy in mucositis patients.

The compositions realized in accordance with embodiments of the present disclosure can find utility in treatment of oral mucositis, oral ulcers, esophagitis, microbial infections, radiation induced esophagitis, pharyngitis, and the like oral, pharyngeal, oropharyngeal and esophageal diseases/conditions. The compositions of the present disclosure also provide improved pain relief in radiation induced oral mucositis, and may reduce the usage of opioids such as Morphine. It could be noted that the components of the compositions realized in accordance with embodiments of the present disclosure exhibit high degree of functional reciprocity by targeting different pathways and consequently, afford unique treatment options oral mucositis, oral ulcers, esophagitis, pharyngitis, and the like oral, pharyngeal, oropharyngeal and esophageal diseases/conditions.

Accordingly, an embodiment of the present disclosure provides a method of treatment of an oral, pharyngeal, oropharyngeal and esophageal condition in a subject, said method comprising administering to a subject in need thereof an effective amount of a composition comprising Lidocaine or salt or hydrate or solvate thereof, L-Carnosine or salt or hydrate or solvate thereof and dexpanthenol or salt or hydrate or solvate thereof. In an embodiment, the composition is formulated as an oral formulation. The oral, pharyngeal, oropharyngeal and esophageal condition may be ulcer, ulcer mediated pain, oral mucositis and the like conditions associated with pain and/or caused by or associated with heightened oxidative stress.

Further embodiment of the present disclosure provides a pharmaceutical composition for use in treatment of an oral, pharyngeal, oropharyngeal and esophageal condition, said composition comprising Lidocaine or salt or hydrates or solvates thereof and Melatonin or salt or hydrates or solvates thereof. The oral, pharyngeal, oropharyngeal and esophageal condition may be ulcer, ulcer mediated pain, oral mucositis and the like conditions associated with pain and/or caused by or associated with heightened oxidative stress.

Yet another embodiment of the present disclosure provides use of a pharmaceutical composition for manufacture of a medicament for treatment of an oral, pharyngeal, oropharyngeal and esophageal condition, said composition comprising Lidocaine or salt or hydrates or solvates thereof and Melatonin or salt or hydrates or solvates thereof. The oral, pharyngeal, oropharyngeal and esophageal condition may be ulcer, ulcer mediated pain, oral mucositis and the like conditions associated with pain and/or caused by or associated with heightened oxidative stress.

Further embodiment of the present disclosure provides a pharmaceutical composition for treatment of an oral, pharyngeal, oropharyngeal and esophageal condition, said composition comprising Lidocaine or salt or hydrates or solvates thereof and Melatonin or salt or hydrates or solvates thereof. The oral, pharyngeal, oropharyngeal and esophageal condition may be ulcer, ulcer mediated pain, oral mucositis and the like conditions associated with pain and/or caused by or associated with heightened oxidative stress.

The compositions of the present disclosure affords increased therapeutic effects, and reduced adverse effects, making these pharmaceutical compositions extremely effective therapeutics, especially in the treatment of oral, pharyngeal, oropharyngeal and esophageal diseases/conditions. Therapeutic levels of the combined drugs will vary from individual to individual and progression stage of disease. The combination medications in the appropriate amounts and intervals effective to treat oral, pharyngeal, oropharyngeal and esophageal disorders or diseases will necessarily be monitored both clinically and chemically by the medical experts or trained physicians.

Further, the patient may receive the specific dosage over a period of weeks, months, or years. For example, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years and the like.

The choice of appropriate dosages for the drugs used in combination therapy according to the present disclosure can be determined and optimized by the skilled artisan, e.g., by observation of the patient, including the patient's overall health, the response to the combination therapy, and the like. Optimization, for example, may be necessary if it is determined that a patient is not exhibiting the desired therapeutic effect or conversely, if the patient is experiencing undesirable or adverse side effects that are too many in number or are of a troublesome severity.

It is especially advantageous to formulate compositions of the present disclosure in unit dosage form for ease of administration and uniformity of dosage. The specifications of the dosage unit forms of the present disclosure are dependent on the unique characteristics of the composition and the particular therapeutic effect to be achieved. Dosages can further be determined by reference to the usual dose and manner of administration of the ingredients. Suitable pharmaceutical compositions and dosage forms may be prepared using conventional methods known to those in the field of pharmaceutical formulation and described in the pertinent texts and literature, e.g., in Remington: The Science and Practice of Pharmacy (Easton, Pa.: Mack Publishing Co., 1995).

It is advantageous to use drug delivery systems (DDS) as devices that can transport and release the therapeutic agents to oral sites at certain rates usually composed of the carriers and associated therapeutics. DDS provides local drug administration and controlled drug release, with fewer side effects. In an embodiment, the oral formulation can be delivered using bio-adhesive devices like varnish, gels, chips, Patches/films/strips, tablets, nano/micro particles, micro/nano sphere, nanofiber, Polymeric microspheres, nano capsule, hydrogel, dendrimer, films, in-situ gel/implants, adhesive gel/patches, adhesive ointment, smart material such like bio-trigged and stimuli-responsive materials. The DDS could react to specific conditions of oral cavity such as pH, temperature, enzymes, and provide more accurate drug delivery.

In certain embodiments, mucoadhesive drug delivery system using polymers such as hydrogel with mucosal adhesiveness is employed for increasing the residence time of the dosage form in the oral cavity, Poly(acrylic acid), Acrylic-grafted starch, Carbopol 934P, polyisobutylene, Alginate-Mg, Al-silicate, and the likes.

In addition, the composition can use one more permeation enhancers to increases the membrane permeation rate or absorption rate. Non-limiting examples include sodium glycocholate, sodium deoxycholate, sodium taurocholate, sodium glycodeoxycholate, sodium glycodeoxycholate, sodium lauryl sulphate, polyoxyethylene, polyoxyethylene-9-laurylether, polyoxythylene-20-cetylether, benzalkonium chloride, oleic acid, capric acid, lauric acid/propylene glycol, methyloleate, lysophosphatidylcholine, phosphatidylcholi, EDTA, citricacid, Sodium salicylate, methoxy salicylates and the likes.

Examples

Fatty Acid Derivatives

Scheme I: Synthesis of 4-((1,3-bis(octanoyloxy)propan-2-yl)oxy)-4-oxobutanoic acid (diglyceryl capryl succinate)

SCHEME 1

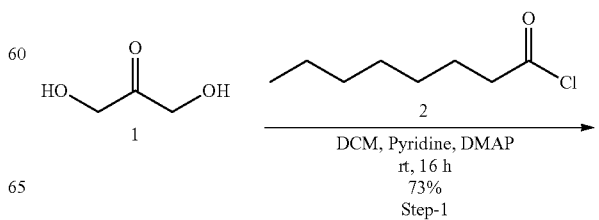

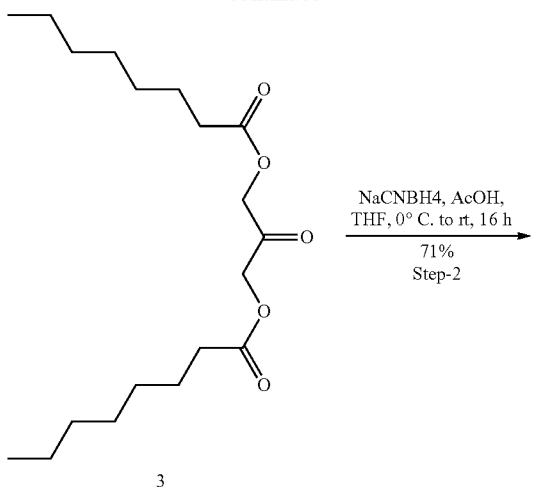

3

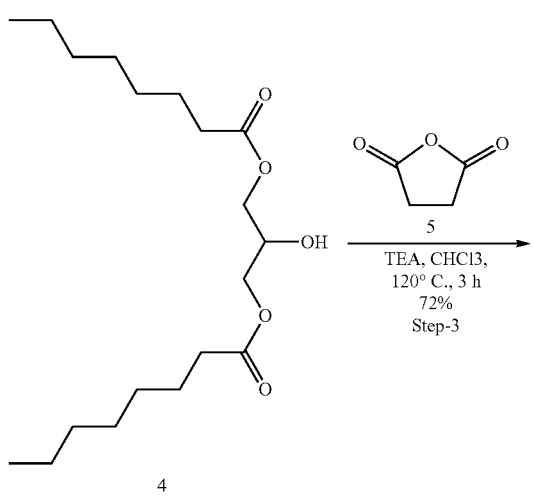

4

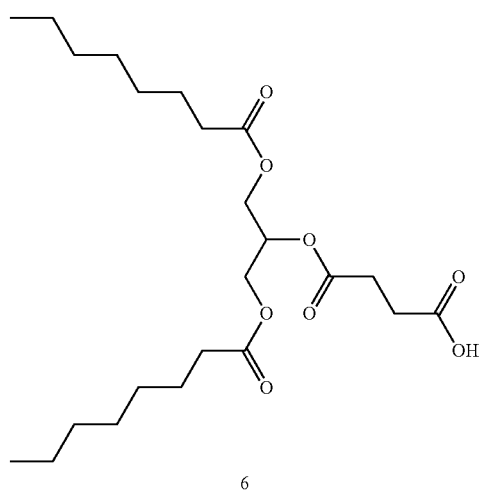

6

Step 1: Synthesis of 2-oxopropane-1,3-diyl dioctanoate (3): To an ice cold solution of 1,3-dihydroxypropan-2-one (1, 25.0 g, 0.277 mol) in dichloromethane (500 mL) was added 4-dimethylaminopyridine (10.17 g, 0.083 mol) and pyridine (49.2 mL, 0.610 mol) and stirred for next 5 min. To the above mixture octanoyl chloride (2, 105.4 mL, 0.610 mol) was added dropwise at 0° C., and the reaction mixture was stirred at room temperature for 16 h. After completion, reaction mixture was filtered; the solid was washed with dichloromethane (100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was purified by silica gel (100-200 mesh) column chromatography eluting with 10% ethyl acetate in hexanes to afford the desired product as white solid. Yield: 70.0 g, 73%. MS (ESI) m/z 343.19[M+1]$^+$; $^1$H NMR (400 MHz, DMSO-d6); δ4.84 (s, 4H), 2.37 (t, J=7.2 Hz, 4H), 1.45-1.62 (m, 4H), 1.15-1.35 (m, 16H), 0.78-0.92 (m, 6H).

Step 2: Synthesis of 2-hydroxypropane-1, 3-diyl dioctanoate (4): To an ice cold solution of 2-oxopropane-1,3-diyl dioctanoate (3, 70.0 g, 0.204 mol) in THF (1000 mL) was added drop wise acetic acid (15 mL), followed by the portion wise addition of sodium cyanoborohydride (15.43 g, 0.245 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude thus obtained was purified by silica gel (100-200 mesh) column chromatography eluting with 12 to 15% ethyl acetate in hexanes to afford the desired product 4 as yellow liquid. Yield: 50.0 g, 71%. MS (ESI)– m/z 345.29[M+1]$^+$; $^1$H NMR (400 MHz, DMSO-d6); δ 5.25 (d, J=5.2 Hz, 1H), 3.92-4.03 (m, 4H), 3.81-3.90 (m, 1H), 2.29 (t, J=7.6 Hz, 4H), 1.45-1.59 (m, 4H), 1.12-1.35 (m, 16H), 0.85 (t, J=6.8 Hz, 6H).

Step 3: Synthesis of 4-((1,3-bis(octanoyloxy)propan-2-yl)oxy)-4-oxobutanoic acid (6): To a solution of 2-hydroxypropane-1,3-diyl dioctanoate (4, 50.0 g, 0.145 mol) in chloroform (200 mL), dihydrofuran-2,5-dione (5, 17.44 g, 0.174 mol) and triethylamine (30.0 mL, 0.218 mol) were added at room temperature. The reaction mixture was stirred at 120° C. for 3 h. After completion, reaction mixture was diluted with water (200 mL) and extracted with 1, 2 dichloromethane (3×200 mL). The organic layer was separated, dried over anhydrous sodium sulfate and concentrated under reduced pressure. The crude thus obtained was purified by silica gel (100-200 mesh) column chromatography eluting with 10 to 15% ethyl acetate in hexanes to afford the desired product 6 as white solid. Yield: 47.0 g, 72%. MS (ESI)– m/z 443.2 [M−1]; $^1$H NMR (400 MHz, DMSO-d6): δ 12.22 (s, 1H), 5.12-5.22 (m, 1H), 4.18-4.25 (m, 2H), 4.09-4.17 (m, 2H), 2.42-2.50 (m, 4H), 2.29 (t, J=7.24 Hz, 4H), 1.44-1.55 (m, 4H), 1.15-1.31 (m, 16H), 0.79-0.90 (m, 6H).

Scheme II: Synthesis of 4-((1,3-bis(dodecanoyloxy) propan-2-yl)oxy)-4-oxobutanoic acid (diglyceryl lauryl succinate)
SCHEME II
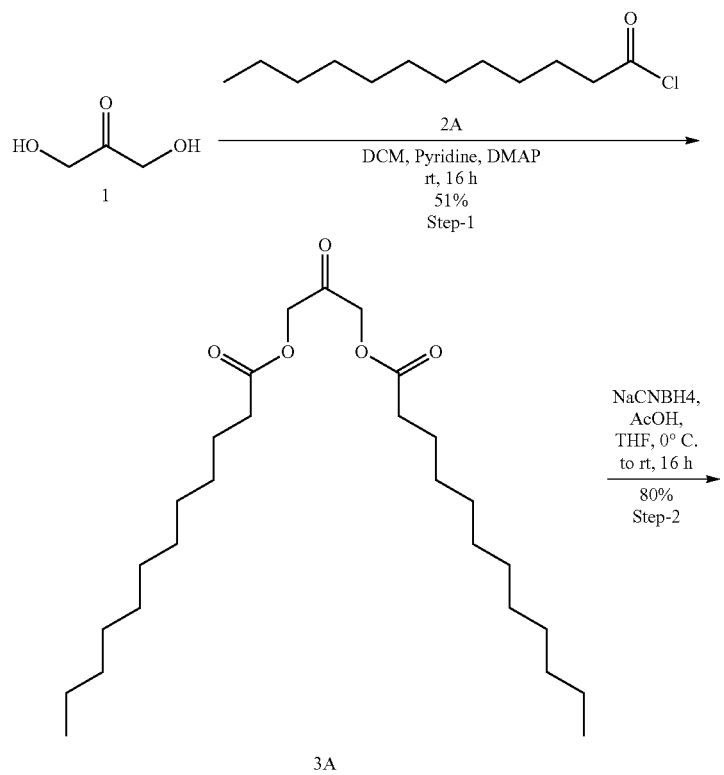
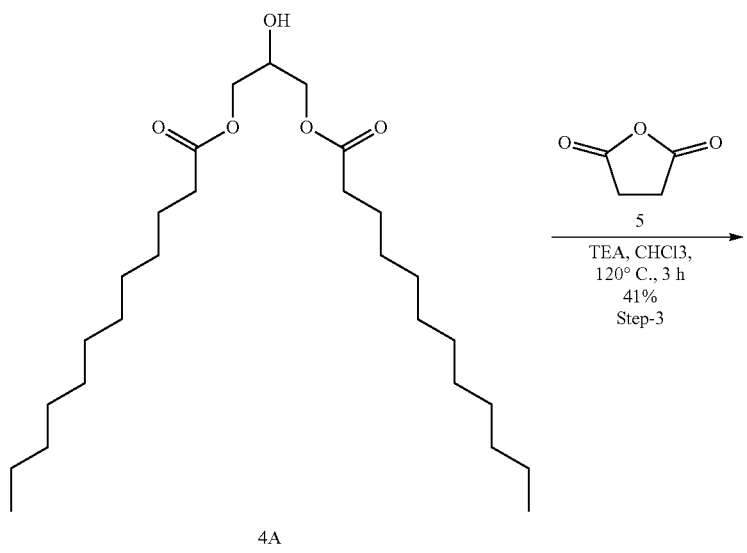

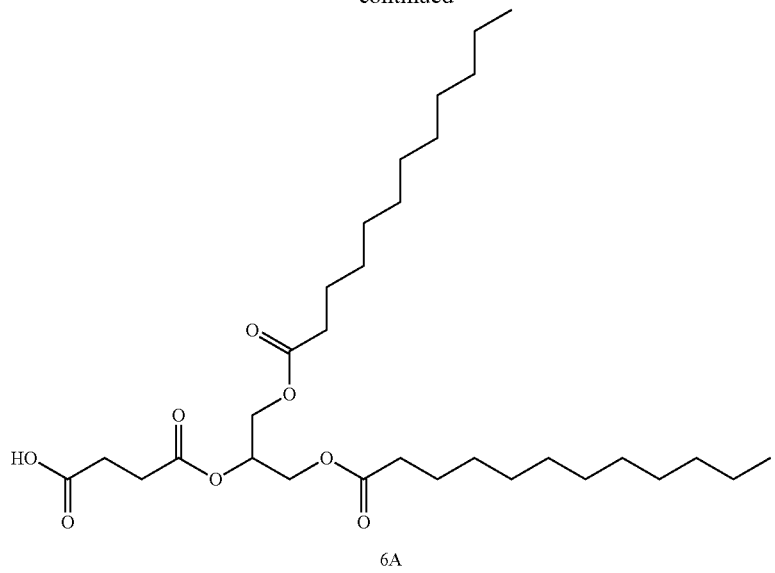 [SMILES: CCCCCCCCCCCC(=O)OCC(COC(=O)CCCCCCCCCCC)OC(=O)CCC(=O)O]

6A

Step 1: Synthesis of 2-oxopropane-1,3-diyl didodecanoate (3A): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above mixture dodecanoyl chloride 2A (218.50 g, 1.167 mol) was added dropwise at 0° C. and the reaction mixture was stirred at room temperature for 16 h. After completion, reaction mixture was filtered; the solid was washed with dichloromethane 100 mL), filtrate was washed with brine (200 mL), saturated solution of sodium bicarbonate (200 mL) and 0.1 N HCl solution (100 mL). Organic layer was separated and dried over anhydrous sodium sulfate and solvent was removed under reduced pressure to get crude. The crude was triturated with diethyl ether to afford the desired product 3A as white solid. Yield: 78 g, 51%. MS (ESI) m/z 455.37[M+1]$^+$; $^1$H NMR (400 MHz, DMSO-d6)—δ4.74 (s, 4H), 2.43 (m, 4H), 1.64 (m, 4H), 1.55-1.25 (m, 32H), 0.87 (m, 6H).

Step 2: Synthesis of 2-hydroxypropane-1, 3-diyl didodecanoate (4A): To an ice cold solution of 2-oxopropane-1,3-diyl didodecanoate 3A (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4A as white solid. Yield: 60.0 g, 80%. MS (ESI); m/z 457.48[M+1]$^+$; $^1$H NMR (400 MHz, DMSO-d6)—δ 5.26 (d, J=5.2 Hz, 1H), 3.92-3.98 (m, 4H), 2.28 (m, 4H), 1.50 (m, 4H), 1.23 (m, 33H), 0.83 (m, 6H).

Step 3: Synthesis of 4-((1, 3-bis(dodecanoyloxy)propan-2-yl)oxy)-4-oxobutanoic acid (6A): To a solution of 2-hydroxypropane-1,3-diyl didodecanoate 4A (40.0 g, 0.087 mol) in chloroform (200 mL), dihydrofuran-2,5-dione 5 (10.50 g, 0.105 mol) and triethylamine (18.50 mL, 0.131 mol) were added at room temperature. The reaction mixture was stirred at 120° C. for 3 h. After completion, reaction mixture was diluted with water (200 mL) and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 25 to 30% ethyl acetate in hexanes to afford the desired product 6A as white solid. Yield: 20.0 g, 41%. MS (ESI) m/z 555.40[M−1]; $^1$H NMR (400 MHz, DMSO-d6) δ 12.30 (s, 1H), 5.17 (m, 1H), 4.18-4.25 (m, 4H), 2.50-2.47 (m, 8H), 1.23-1.25 (m, 36H), 0.83 (m, 6H).

Scheme III: Synthesis of (E)-4-((1,3-bis(dodecanoyloxy)propan-2-yl)oxy)-4-oxobut-2-enoic acid (diglycervl lauryl fumarate)

SCHEME III

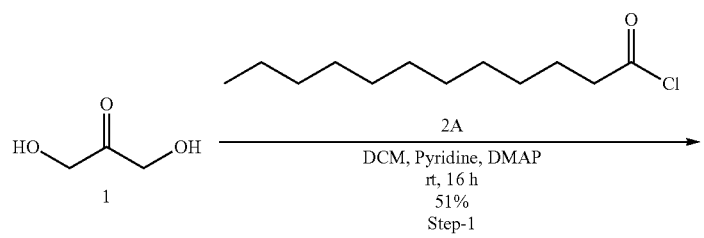

-continued
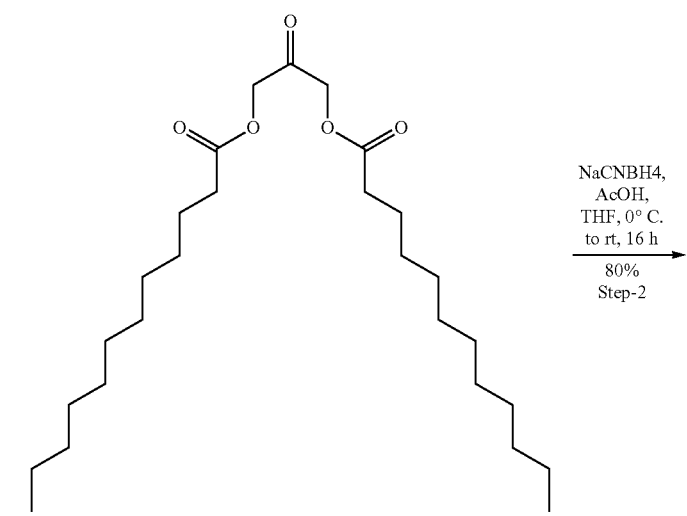
3*
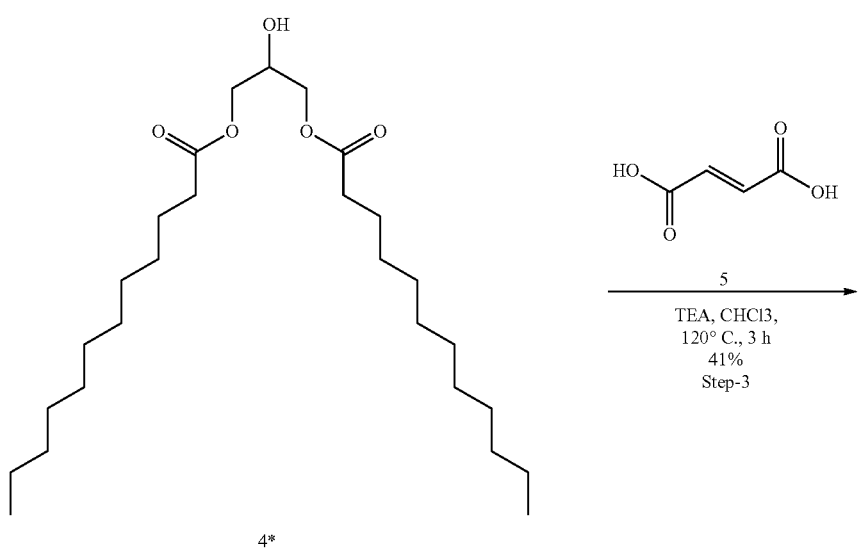
4*
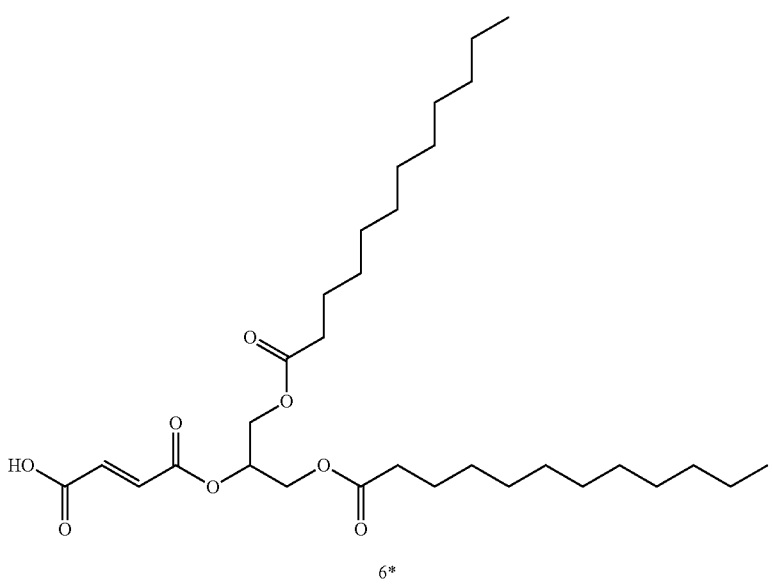 [SMILES: CCCCCCCCCCCC(=O)OCC(COC(=O)CCCCCCCCCCC)OC(=O)/C=C/C(=O)O]
6*

Step 1—Synthesis of 2-oxopropane-1,3-diyl didodecanoate (3*): To an ice cold solution of 1,3-dihydroxypropan-2-one (1, 30.0 g, 0.33 mol) in dichloromethane (500 mL) was added 4-dimethylaminopyridine (20.30 g, 0.167 mol) and pyridine (107 mL, 0.1.332 mol) and stirred for next 5 min. To the above reaction mixture dodecanoyl chloride 2 (218.50 g, 1.167 mol) was added dropwise at 0° C. and the reaction mixture was stirred at room temperature for 16 h. After completion, reaction mixture was filtered, the solid was washed with dichloromethane (100 mL), and the filtrate was washed with brine (200 mL), saturated solution of sodium bicarbonate (200 mL) and 0.1 N HCl solution (100 mL). The organic layer was separated, dried over anhydrous sodium sulfate and solvent was removed under reduced pressure to get crude. The crude was triturated with diethyl ether to afford the desired product 3* as white solid. Yield: 78 g, 51%. MS (ESI) m/z 455.37[M+1]+; 1H NMR (400 MHz, DMSO-d6): δ 4.74 (s, 4H), 2.43 (m, 4H), 1.64 (m, 4H), 1.55-1.25 (m, 32H), 0.87 (m, 6H).

Step-2: Synthesis of 2-hydroxypropane-1,3-diyl didodecanoate (4*): To an ice cold solution of 2-oxopropane-1,3-diyl didodecanoate 3 (75.0 g, 0.165 mol) in THF (1000 mL) was added drop wise acetic acid (15 mL) followed by the portion wise addition of sodium cyanoborohydride (12.41 g, 0.198 mol). The reaction mixture was stirred at room temperature for 16 h. After completion, reaction mixture was diluted with water (400 mL) and extracted with ethyl acetate (3×200 mL). The organic layer was separated, dried over anhydrous sodium sulfate and solvent was removed under reduced pressure. The crude was triturated with diethyl ether to afford the desired product 4* as white solid. Yield: 60.0 g, 80%. MS (ESI) m/z 457.48[M+I]$^+$; 1H NMR (400 MHz, DMSO-d6): δ 5.26 (d, J=5.2 Hz, 1H), 3.92-3.98 (m, 4H), 2.28 (m, 4H), 1.50 (m, 4H), 1.23 (m, 33H) and 0.83 (m, 6H).

Step-3: Synthesis of (E)-4-((1,3-bis(dodecanoyloxy)propan-2-yl)oxy)-4-oxobut-2-enoic acid (6*): To an ice-cold solution of 2-hydroxypropane-1,3-diyl didodecanoate 4 (10.0 g, 21.91 mmol) in THF (170 mL) was added fumaric acid 5 (2.54 g, 21.91 mmol), benzoyl chloride (2.5 mL, 21.91 mmol) and DMAP (0.67 g, 5.477 mmol). The resulting mixture was stirred at RT for 16 h. After completion of reaction (TLC monitoring), reaction mixture was concentrated under reduced pressure. The crude was diluted with water (200 mL), adjust pH ~2-3 using 1N-HCl and extracted with 1,2 dichloromethane (3×200 mL). The organic layer was separated, dried over anhydrous sodium sulfate and concentrated under reduced pressure. The crude thus obtained was purified by silica gel (100-200 mesh) column chromatography eluting with 80% ethyl acetate in hexanes to afford the desired product 6* as white solid. Yield: 400 mg, 3.30% (un-optimized yield). LC-MS: m/z 553.64[M−1]; 97.27% purity. 1H NMR (400 MHz, DMSO-d6): δ 13.26 (br s, 1H), 5.17 (d, J=15.8 Hz, 2H), 5.29 (m, 1H), 4.30-4.33 (m, 2H), 4.19-4.23 (m, 2H), 2.28 (m, 4H), 1.48 (m, 4H), 1.22 (m, 32H) and 0.83 (m, 6H).

Non-Limiting Exemplary Compositions

Batch ACGCP200343035A

TABLE 1

Composition for Lidocaine, L-Carnosine and D-Panthenol Oral rinse

| Ingredients | % W/V |
|---|---|
| Lidocaine HCl | 2.0 |
| L-Carnosine | 1.0 |
| D-Panthenol | 5.0 |
| Citric acid anhydrous | 0.1679 |
| Tri Sodium citrate dihydrate | 1.2135 |
| Xylitol powder 90 | 7.5 |
| Glycerol | 5.0 |
| Propylene glycol | 5.0 |
| Benzalkonium chloride | 0.02 |
| Sodium metabisulfite | 0.04 |
| Sodium hyaluronate | 0.2 |
| PVP K30 | 10.0 |
| Water | Qs to 100 |

Method of preparation of Lidocaine, L-Carnosine and D-Panthenol Oral rinse i. Premix 1—Dexpanthenol solution: 10% water of batch quantity was taken in to a compounding vessel and requisite amount of D-Panthenol was added thereto while mixing for 15 minutes using an overhead stirrer.

ii. Premix 2-40% water of batch quantity was taken in a compounding vessel 2 and Citric acid anhydrous, Tri Sodium citrate dihydrate, Lidocaine HCl, L-Carnosine, Xylitol powder 90, Propylene glycol, Sodium metabisulfite, Benzalkonium chloride, Glycerol and PVP K30 was added thereto one after another and stirred for 30 minutes using magnetic stirrer to get a clear solution.

iii. Premix 3—Sodium Hyaluronate solution: 15% water of batch quantity was taken in a compounding vessel 3 and sodium hyaluronate was added thereto while mixing using an overhead stirrer at 600 RPM to get a clear viscous solution.

iv. Premix 1 (Dexpanthenol solution) was then added to the premix 2 and allowed to dissolve completely for 15 minutes.

v. Premix 3 (Sodium Hyaluronate solution) was then mixed with the mixture of premix 1 and premix 2 and allowed to dissolve completely for 30 minutes.

vi. Final volume was then adjusted using the remainder of water and filled into a container.

TABLE 1b

Stability Data of BATCH ACGCP200343035A

| Test parameters | Proposed Specification | Initial | 40° C./75% RH | | |
|---|---|---|---|---|---|
| | | | 1 M | 2 M | 3 M |
| Description | A Clear, slightly yellowish Liquid | C | C | C | C |
| pH | 5.5-7.5 | 6.56 | 6.58 | 6.57 | 6.57 |
| % Assay-Lidocaine HCl | 90.0-110.0% | 103.1 | 97.8 | 102.8 | 100.7 |

TABLE 1b-continued

Stability Data of BATCH ACGCP200343035A

| Test parameters | Proposed Specification | Initial | 40° C./75% RH | | |
|---|---|---|---|---|---|
| | | | 1 M | 2 M | 3 M |
| % Assay-Dexpanthenol | 90.0-110.0% | 105.8 | 103.5 | 100.1 | 102.2 |
| % Assay-L-Carnosine | 90.0-110.0% | 102.9 | 105.2 | 99.6 | 100.0 |
| % Assay - BKC | 93.0-107.0% | — | — | — | 105.4 |
| Related substances. (%, w/v) | | | | | |
| Lidocaine Related Compound H | NMT 0.5% | ND | 0.06 | ND | ND |
| 2,6 Dimethylaniline | NMT 0.5% | ND | ND | ND | ND |
| Any Unspecified degradant related to lidocaine | NMT 0.5% | 0.03 | 0.05 | 0.16 | 0.17 |
| Any Individual highest degradant related to Dexpanthenol | NMT 1.0% | 0.14 | 0.24 | 0.18 | 0.10 |
| Any Individual highest degradant related to L-Carnosine | NMT 1.0% | 0.16 | 0.16 | 0.58 | 0.85 |
| Total Degradants | NMT 3.5 | 1.02 | 1.25 | 1.21 | 1.75 | pH: The pH of the formulation ACGCP200343035A is checked using pH meter (Mettler Toledo, seven compact S210) and the pH was found to be 6.5 ± 0.09.
Density: Density was estimated using densitometer (Mettler Toledo, Density 2Go). The density was found to be 1.074 g/cm³.
Viscosity: Viscosity of oral rinse is measured using Brookfield viscometer using Spindle S00 & UL adopter at room temperature. The formulation was found to be showing Newtonian behavior.

TABLE 1c

| ACG001C0131017B | | | | |
|---|---|---|---|---|
| | Spindle | RPM | Torque | cP |
| Brookfield viscometer DV-II Pro | S00 | 0.5 | 12.7 | 152.4 |
| | | 1.0 | 25.8 | 154.8 |
| | | 1.5 | 38.6 | 154.4 |
| | | 2.0 | 51.2 | 153.6 |
| | | 2.5 | 63.3 | 151.9 |
| | | 3.0 | 75.1 | 150.2 |

Local Anesthetics such as bupivacaine HCl or ropivacaine HCl at therapeutically effective strengths is substituted instead of lidocaine HCl in the following exemplified composition.

TABLE 1d

Composition for bupivacaine, L-Carnosine and D-Panthenol Oral rinse

| Ingredients | % W/V |
|---|---|
| Bupivacaine HCl | 2.5 |
| L-Carnosine | 1.0 |
| D-Panthenol | 5.0 |
| Citric acid anhydrous | 0.1679 |
| Tri Sodium citrate dihydrate | 1.2135 |
| Xylitol powder 90 | 7.5 |
| Glycerol | 5.0 |
| Propylene glycol | 5.0 |
| Benzalkonium chloride | 0.02 |
| Sodium metabisulfite | 0.04 |
| Sodium hyaluronate | 0.2 |
| PVP K30 | 10.0 |
| Water | Qs to 100 |

TABLE 1e

Composition for ropivacaine, L-Carnosine and D-Panthenol Oral rinse

| Ingredients | % W/V |
|---|---|
| Ropivacaine HCl | 2.5 |
| L-Carnosine | 1.0 |
| D-Panthenol | 5.0 |
| Citric acid anhydrous | 0.1679 |
| Tri Sodium citrate dihydrate | 1.2135 |
| Xylitol powder 90 | 7.5 |
| Glycerol | 5.0 |
| Propylene glycol | 5.0 |
| Benzalkonium chloride | 0.02 |
| Sodium metabisulfite | 0.04 |
| Sodium hyaluronate | 0.2 |
| PVP K30 | 10.0 |
| Water | Qs to 100 |

Method of Preparation of Local Anesthetic, L-Carnosine and D-Panthenol Oral Rinse i. Premix 1—Dexpanthenol solution: 10% water of batch quantity was taken in to a compounding vessel and requisite amount of D-Panthenol was added thereto while mixing for 15 minutes using an overhead stirrer.

ii. Premix 2-40% water of batch quantity was taken in a compounding vessel 2 and Citric acid anhydrous, Tri Sodium citrate dihydrate, Local Anesthetic, L-Carnosine, Xylitol powder 90, Propylene glycol, Sodium metabisulfite, Benzalkonium chloride, Glycerol and PVP K30 was added thereto one after another and stirred for 30 minutes using magnetic stirrer to get a clear solution.

iii. Premix 3—Sodium Hyaluronate solution: 15% water of batch quantity was taken in a compounding vessel 3 and sodium hyaluronate was added thereto while mixing using an overhead stirrer at 600 RPM to get a clear viscous solution.
iv. Premix 1 (Dexpanthenol solution) was then added to the premix 2 and allowed to dissolve completely for 15 minutes.
v. Premix 3 (Sodium Hyaluronate solution) was then mixed with the mixture of premix 1 and premix 2 and allowed to dissolve completely for 30 minutes.
vi. Final volume was then adjusted using the remainder of water and filled into a container.

Batch ACGCP200343032A

Oral rinse was prepared using the composition as provided in Table 2 below.

TABLE 2

Composition for Lidocaine, L-Carnosine and D-Panthenol Oral rinse

| Ingredients | % W/V |
| --- | --- |
| Lidocaine HCl | 2.0% |
| L-Carnosine | 1.0% |
| D-Panthenol | 5.0% |
| Citric acid anhydrous | 0.1679% |
| Tri Sodium citrate dihydrate | 1.2135% |
| Xylitol powder 90 | 7.5% |
| Glycerol | 5.0% |
| Propylene glycol | 10.0% |
| PVP K30 | 10.0% |
| Water | Qs to 100% |

Method of Preparation of Lidocaine, L-Carnosine and D-Panthenol Oral Rinse
i. Premix 1—Dexpanthenol solution: 10% water of batch quantity was taken in to a compounding vessel and requisite amount of D-panthenol was added thereto while mixing for 15 minutes using an overhead stirrer.
ii. Premix 2-60% water of batch quantity was taken in a compounding vessel 2 and Citric acid anhydrous, Tri Sodium citrate dihydrate, Lidocaine HCl, L-Carnosine, Xylitol powder 90, Propylene glycol, Glycerol and PVP K30 was added thereto one after another and stirred for 30 minutes using magnetic stirrer to get a clear solution.
iii. Premix 1 (Dexpanthenol solution) was then added to the premix 2 and allowed to dissolve completely for 15 minutes.
iv. Final volume was then adjusted using the remainder of water and filled into a container.

Batch ACGCP200343034A

TABLE 3

Composition for Lidocaine, L-Carnosine and D-Panthenol Oral rinse ACGCP200343034A

| S. No. | Ingredients | % W/V |
| --- | --- | --- |
| 01 | Lidocaine HCl | 2.0 |
| 02 | L-Carnosine | 1.0 |
| 03 | D-Panthenol | 5.0 |
| 04 | Citric acid anhydrous | 0.1679 |
| 05 | Tri Sodium citrate dihydrate | 1.2135 |
| 06 | Xylitol powder 90 | 7.5 |
| 07 | Glycerol | 5.0 |
| 08 | Propylene glycol | 5.0 |
| 09 | Benzalkonium chloride | 0.02 |
| 10 | Sodium metabisulfite | 0.04 |
| 11 | Sodium hyaluronate | 0.2 |
| 12 | PVP K30 | 10.0 |
| 13 | Water | Qs to 100 |

Batch ACGCP200343008A

Oral rinse was prepared using the composition as provided in Table 4 below:

TABLE 4

Compositions for Lidocaine, L-Carnosine and D-Panthenol Oral rinses

| Ingredients | % W/V |
| --- | --- |
| Lidocaine HCl | 2.0% |
| Melatonin | 0.1% |
| Citric acid monohydrate | 1.2725% |
| Tri Sodium citrate dihydrate | 0.9929% |
| L-Carnosine | 1.0% |
| D-Panthenol | 5.0% |
| Xylitol powder | 7.5% |
| Glycerol | 5.0% |
| Propylene glycol | 10.0% |
| PVP K30 | 10.0% |
| Sodium hyluronate | 0.2% |
| Water | Qs to 100% |

Method of Preparation of Lidocaine, L-Carnosine and D-Panthenol Oral Rinse
i. Premix 1—Dexpanthenol solution: 10% water of batch quantity was taken in to a compounding vessel and requisite amount of D-Panthenol was added thereto while mixing for 15 minutes using an overhead stirrer.
ii. Premix 2-50% water of batch quantity was taken in a compounding vessel 2 and Citric acid anhydrous, Tri Sodium citrate dihydrate, Lidocaine HCl, L-Carnosine, Xylitol powder, Glycerol and PVP K30 was added thereto one after another and stirred for 30 minutes using magnetic stirrer to get a clear solution.
iii. Premix 3—Sodium Hyaluronate solution: 15% water of batch quantity was taken in a compounding vessel 3 and sodium hyaluronate was added thereto while mixing using an overhead stirrer at 600 RPM to get a clear viscous solution.
iv. Premix 4—Melatonin solution: Propylene glycol was taken in a compounding vessel and Melatonin was dissolved therein while stirring using a magnetic stirrer for 15 minutes.
v. Premix 1 (Dexpanthenol solution) and premix 4 (Melatonin solution) were then added to the premix 2 and allowed to dissolve completely for 15 minutes.
vi. Premix 3 (Sodium Hyaluronate solution) was then mixed with the mixture of premix 1 and premix 2 and allowed to dissolve completely for 30 minutes.
vii. Final volume was then adjusted using the remainder of water and filled into a container.

TABLE 5

Assay and RS of ACGCP200343008A

| Batch No. | DOA | Time point | Assay % | | | % of degradants | | | |
|---|---|---|---|---|---|---|---|---|---|
| | | | Lidocaine | DGLF | Melatonin | RRT 1.61 | 2.46 | 1.51 | Total |
| ACGCP200343008A | 07 Apr. 2021 | Initial | 98.5 | N/A | 102.0 | 0.006 | 0.020 | BDL | 0.026 |

TABLE 6

Analysis results for D-Panthenol and L-Carnosine.

| Batch No. | DOA | Time point | Assay % | | Assay % | | | % of degradants | | | |
|---|---|---|---|---|---|---|---|---|---|---|---|
| | | | D-Panthenol | L-Carnosine | Lidocaine | DGLF | Melatonin | RRT 1.61 | RRT 2.46 | RRT 2.51 | Total |
| ACGCP200343008A | 07 Apr. 2021 | Initial | 111.2 | 103.6 | 98.5 | N/A | 102.0 | 0.006 | 0.020 | BDL | 0.026 |

Batch ACGCP200343011A

Oral rinse was prepared using the composition as provided in Table 7 below.

TABLE 7

Composition for Lidocaine, L-Carnosine and D-Panthenol Oral rinse

| Ingredients | % W/V |
|---|---|
| Lidocaine HCl | 2.0% |
| Citric acid monohydrate | 1.2725% |
| Tri Sodium citrate dihydrate | 0.9929% |
| L-Carnosine | 1.0% |
| D-Panthenol | 5.0% |
| Xylitol powder | 7.5% |
| Glycerol | 5.0% |
| Propylene glycol | 10.0% |
| PVP K30 | 10.0% |
| Sodium hyaluronate | 0.2% |
| Water | Qs to 100% |

Oral rinse formulation was prepared using the method as described above (for BATCH ACGCP200343035A). Assay & RS of ACGCP200343011A is provided in a Table 8 below.

TABLE 8

Assay & RS of ACGCP200343011A

| Batch No. | Time point | Assay % | | | % Of degradants | | | |
|---|---|---|---|---|---|---|---|---|
| | | Lidocaine | DGLF | Melatonin | RRT 1.61 | 2.46 | 1.51 | Total |
| ACGCP200343011A | Initial | 104.3 | N/A | N/A | 0.004 | 0.005 | BDL | 0.009 |

Batch ACGCP200343012A

TABLE 9

Composition for melatonin Oral rinse ACGCP200343012A

| S. No. | Ingredients | % W/V |
|---|---|---|
| 01 | Melatonin | 0.1% |
| 02 | Chlorhexidine Diacetate | 0.13% |
| 03 | D-Panthenol | 5.0% |
| 04 | Xylitol powder | 7.5% |
| 05 | Glycerol | 5.0% |
| 06 | Propylene glycol | 10.0% |
| 07 | PVP K30 | 10.0% |
| 08 | Sodium hyaluronate | 0.2% |
| 09 | HCl | Qs to pH 4.0 |
| 10 | Water | Qs to 100% |

TABLE 10

Assay & RS for ACGCP200343012A

| | | | Assay % | | | % of degradants | | | | |
|---|---|---|---|---|---|---|---|---|---|---|
| Sample ID | Time DOA | point | Description | Lidocaine | DGLF | Melatonin | RRT 1.61 | RRT 2.46 | RRT 2.51 | RRT 3.21 | % Total |
| N/A | 10 Apr. 2021 | Initial | light yellow colour solution | N/A | N/A | 101.4 | 0.010 | 0.020 | BDL | BDL | 0.030 |

Batch ACGCP200343013A

Oral rinse was prepared using the composition as provided in Table 11 below.

TABLE 11

Composition for Lidocaine, L-Carnosine and D-Panthenol Oral rinse

| Ingredients | % W/V |
|---|---|
| Lidocaine HCl | 2.0% |
| Melatonin | 0.1% |
| Citric acid anhydrous | 1.5066% |
| Tri Sodium citrate dihydrate | 0.6344% |
| L-Carnosine | 1.0% |
| D-Panthenol | 5.0% |
| Xylitol powder | 7.5% |
| Glycerin | 5.0% |
| Propylene glycol | 10.0% |
| PVP K30 | 10.0% |
| Sodium hyaluronate | 0.2% |
| Water | Qs to 100% |

Oral rinse formulation was prepared using the method as described above (for BATCH ACGCP200343008A).

Batch ACGCP200343014A

Oral rinse formulation was prepared using the composition as provided in Table 12 below.

TABLE 12

Composition for Lidocaine, L-Carnosine and D-Panthenol Oral rinse

| Ingredients | % W/V |
|---|---|
| Lidocaine HCl | 2.0% |
| Citric acid anhydrous | 1.5066% |
| Tri Sodium citrate dihydrate | 0.6344% |
| L-Carnosine | 1.0% |
| D-Panthenol | 5.0% |
| Xylitol powder | 7.5% |
| Glycerin | 5.0% |
| Propylene glycol | 10.0% |
| PVP K30 | 10.0% |
| Sodium hyaluronate | 0.2% |
| Water | Qs to 100% |

Oral rinse formulation was prepared using the method as described above (for BATCH ACGCP200343035A). Assay & RS of ACGCP200343013A & ACGCP200343014A is provided in a Table 13 below.

TABLE 13

Assay and RS for ACGCP200343013A & ACGCP200343014A

| Batch No. | Time point DOA | Description | Assay % CLX-GEN-G005-C01 | Assay % CLX-GEN-G006-C01 | MT RC A 0.88 | LD DMA | LD RC H 5.50 | RRT 1.61 | RRT 6.94 | |
|---|---|---|---|---|---|---|---|---|---|---|
| | Lidocaine API B #LDH/120018 + Melatonin API B# MLT/520004 | | 99.9 | 99.4 | 0.01 | 0.001 | ND | 0.01 | BDL | 0.021 |
| ACGCP200343013A | Initial 22 Apr. 2021 | Clear, off white solution | 105.0 | 106.0 | 0.01 | BDL | BDL | 0.01 | 0.01 | 0.02 |
| ACGCP200343014A | Initial 22 Apr. 2021 | Clear, off white solution | 104.6 | N/A | BDL | BDL | BDL | BDL | 0.01 | 0.01 |

TABLE 14

ACGCP200343013A & ACGCP200343014A Stability batch 1 Month RS results

| Batch No. | Conditions | MLT · RC A | 0.07 | 0.10 | 0.11 | 0.13 | 0.15 | 0.24 | 0.63 | 0.78 | Total |
|---|---|---|---|---|---|---|---|---|---|---|---|
| ACGCP200343013A | 40° C./75%RH- 3M | 1.19 | 0.22 | 0.10 | 0.16 | 0.04 | 0.19 | 0.17 | ND | 0.60 | 2.67 |
| | 30° C./65%RH- 3M | 0.78 | 0.12 | 0.06 | 0.06 | ND | 0.15 | 0.16 | ND | 0.65 | 1.98 |
| | 25° C./60%RH- 3M | 0.56 | 0.06 | 0.04 | 0.04 | ND | 0.10 | 0.11 | ND | 0.59 | 1.50 |
| | 2-8° C.-3M | 0.18 | 0.02 | 0.01 | 0.04 | ND | 0.03 | 0.04 | ND | 0.57 | 0.89 |
| ACGCP200343014A | 40° C./75% RH- 3M | ND | ND | 0.06 | ND | ND | ND | ND | 0.04 | ND | 0.10 |
| | 30° C./65% RH- 3M | ND | ND | 0.05 | ND | ND | ND | ND | 0.04 | ND | 0.09 |
| | 25° C./60% RH- 3M | ND | ND | 0.04 | ND | ND | ND | ND | 0.04 | ND | 0.08 |
| | 2-8° C.-3M | ND | ND | 0.01 | ND | ND | ND | ND | 0.03 | ND | 0.04 |

TABLE 15

ACGCP200343013A & ACGCP200343014A Stability batch 3 Month Assay results

| Batch No. | Condition | Melatonin | Lidocaine | D-Panthenol | L-Carnosine |
|---|---|---|---|---|---|
| ACGCP200343013A | 40° C.-1M | 92.6 | 102.8 | 97.9 | 95.7 |
| | 30° C.-1M | 94.6 | 101.3 | 101.6 | 98.7 |
| | 25° C.-1M | 95.2 | 100.7 | 101.8 | 98.9 |
| | 2-8° C.-1M | 97.9 | 99.8 | 101.9 | 98.3 |
| ACGCP200343014A | 40° C.-1M | NA | 99.7 | 96.2 | 94.9 |
| | 30° C.-1M | NA | 100.1 | 99.2 | 97.6 |
| | 25° C.-1M | NA | 99.9 | 100.2 | 99.2 |
| | 2-8° C.-1M | NA | 100.3 | 100.2 | 98.2 |

Batch ACGCP200343015A

Oral rinse formulation was prepared using the composition as provided in Table 16 below. Oral rinse formulation was prepared following the method as described above.

TABLE 16

Composition for Lidocaine, L-Carnosine and D-Panthenol Oral rinse

| Ingredients | % W/V |
|---|---|
| Lidocaine HCl | 2.0% |
| Melatonin | 0.1% |
| Citric acid anhydrous | 1.5066% |
| Tri Sodium citrate dihydrate | 0.6344% |
| L-Carnosine | 1.0% |
| D-Panthenol | 5.0% |
| Xylitol powder | 7.5% |
| Glycerol | 5.0% |
| Propylene glycol | 10.0% |
| Benzyl alcohol | 2.0% |
| PVP K30 | 10.0% |
| Sodium hyaluronate | 0.2% |
| Water | Qs to 100% |

Batch ACGCP200343016A

Oral rinse formulation was prepared using the composition as provided in Table 17 below. Oral rinse formulation was prepared following the method as described above.

TABLE 17

Composition for Lidocaine, L-Carnosine and D-Panthenol Oral rinse

| Ingredients | % W/V |
|---|---|
| Lidocaine HCl | 2.0% |
| Melatonin | 0.1% |
| Citric acid anhydrous | 1.5066% |
| Tri Sodium citrate dihydrate | 0.6344% |
| L-Carnosine | 1.0% |
| D-Panthenol | 5.0% |
| Xylitol powder | 7.5% |
| Glycerol | 5.0% |
| Propylene glycol | 10.0% |
| Methyl paraben | 0.1% |
| PVP K30 | 10.0% |
| Sodium hyaluronate | 0.2% |
| Water | Qs to 100% |

Batches ACGCP200343017A, ACGCP200343020A & ACGCP200343023A

TABLE 18

Composition for Lidocaine, and melatonin Oral rinse

| S. No. | Ingredients | ACGCP200343017A | ACGCP200343020A % W/V | ACGCP200343023A |
|---|---|---|---|---|
| 01 | Lidocaine HCl | 2.0% | 2.0% | 2.0% |
| 02 | Melatonin | 0.1% | 0.1% | 0.1% |
| 03 | Citric acid anhydrous | 0.5192% | 0.5192% | 0.5192% |
| 04 | Tri Sodium citrate dihydrate | 0.6757% | 0.6757% | 0.6757% |
| 05 | Xylitol powder 90 | 7.5% | 7.5% | 7.5% |
| 06 | Glycerol | 5.0% | 5.0% | 5.0% |
| 07 | Propylene glycol | 10.0% | 10.0% | 10.0% |
| 08 | Benzyl alcohol | 2.0% | — | — |
| 09 | PVP K30 | 10.0% | 10.0% | 10.0% |
| 10 | Sodium hyaluronate | 0.2% | 0.2% | 0.2% |
| 12 | Water | Qs to 100% | Qs to 100% | Qs to 100% |
| Adjust pH | | 4.5 | 4.5 | 5.5 |

Batches ACGCP200343018A, 21A & 24A

Oral rinse formulations were prepared using the compositions as provided in Table 19 below. Oral rinse formulations were prepared following the method as described above.

TABLE 19

Composition for Lidocaine, L-Carnosine and D-Panthenol Oral rinse

| S. No. | Ingredients | ACGCP200343018A | ACGCP200343021A % W/V | ACGCP200343024A |
|---|---|---|---|---|
| 01 | Lidocaine HCl | 2.0% | 2.0% | 2.0% |
| 02 | Melatonin | 0.1% | 0.1% | 0.1% |
| 03 | Citric acid anhydrous | 0.5192% | 0.5192% | 0.5192% |
| 04 | Tri Sodium citrate dihydrate | 0.6757% | 0.6757% | 0.6757% |
| 05 | L-Carnosine | 1.0% | 1.0% | 1.0% |
| 06 | Xylitol powder 90 | 7.5% | 7.5% | 7.5% |
| 07 | Glycerol | 5.0% | 5.0% | 5.0% |
| 08 | Propylene glycol | 10.0% | 10.0% | 10.0% |
| 09 | Benzyl alcohol | 2.0% | — | — |
| 10 | PVP K30 | 10.0% | 10.0% | 10.0% |
| 12 | Sodium hyaluronate pH | 0.2% | 0.2% | 0.2% |
| 13 | Water | Qs to 100% | Qs to 100% | Qs to 100% |
| pH Adj | | 4.5 | 4.5 | 5.5 |

Batch ACGCP200343019A, 22A & 25A

Oral rinse formulations were prepared using the compositions as provided in Table 20 below. Oral rinse formulations were prepared following the method as described above.

TABLE 20

Composition for Lidocaine, L-Carnosine and D-Panthenol Oral rinse

| S. No. | Ingredients | ACGCP200343019A | ACGCP200343022A % W/V | ACGCP200343025A |
|---|---|---|---|---|
| 01 | Lidocaine HCl | 2.0% | 2.0% | 2.0% |
| 02 | Melatonin | 0.1% | 0.1% | 0.1% |
| 03 | Citric acid anhydrous | 0.5192% | 0.5192% | 0.5192% |
| 04 | Tri Sodium citrate dihydrate | 0.6757% | 0.6757% | 0.6757% |
| 05 | L-Carnosine | 1.0% | 1.0% | 1.0% |
| 06 | D-Panthenol | 5.0% | 5.0% | 5.0% |
| 07 | Xylitol powder 90 | 7.5% | 7.5% | 7.5% |
| 08 | Glycerol | 5.0% | 5.0% | 5.0% |
| 09 | Propylene glycol | 10.0% | 10.0% | 10.0% |
| 10 | Benzyl alcohol | 2.0% | — | — |
| 12 | PVP K30 | 10.0% | 10.0% | 10.0% |
| 13 | Sodium hyaluronate | 0.2% | 0.2% | 0.2% |
| 14 | Water | Qs to 100% | Qs to 100% | Qs to 100% |
| Adj pH | | 4.5 | 4.5 | 5.5 |

TABLE 21 stability of ACGCP200343017A to ACGCP200343025A
ACGCP200343017A to ACGCP200343025A Initial results

| Batch No. | DOA | Time point | pH | BZA | Assay % D-Panthenol | Assay % L-Carnosine | Assay % Lidocaine | Assay % Melatonin | % of degradants (w.r.t MLT) LDRCH |
|---|---|---|---|---|---|---|---|---|---|
| ACGCP200343017A | 2 Apr. 2021 | Initial | NT | 103 | NA | NA | 99.6 | 97.5 | 0.01 |
| ACGCP200343018A | 2 Apr. 2021 | Initial | NT | 101 | NA | 103.7 | 97.8 | 93.5 | 0.08 |
| ACGCP200343019A | 2 Apr. 2021 | Initial | NT | 103 | 99.8 | 102.2 | 98.4 | 96.7 | 0.09 |
| ACGCP200343020A | 2 Apr. 2021 | Initial | NT | NA | NA | NA | 97.8 | 97.7 | 0.01 |
| ACGCP200343021A | 2 Apr. 2021 | Initial | NT | NA | NA | 103.1 | 97.2 | 96.4 | 0.07 |
| ACGCP200343022A | 2 Apr. 2021 | Initial | NT | NA | 99 | 102.7 | 97.2 | 97.5 | 0.09 |
| ACGCP200343023A | 2 Apr. 2021 | Initial | NT | NA | NA | NA | 101 | 99.4 | 0.02 |
| ACGCP200343024A | 2 Apr. 2021 | Initial | NT | NA | NA | 104.5 | 97.2 | 99.6 | 0.18 |
| ACGCP200343025A | 2 Apr. 2021 | Initial | NT | NA | 97 | 104.9 | 97.3 | 96.7 | 0.19 |

| Batch No. | MLT RCA | DMA | RRT 0.23 | RRT 0.27 | RRT 0.33 | RRT 0.35 | RRT 0.38 | RRT 0.42 | RRT 0.47 | RRT 0.51 | % Total |
|---|---|---|---|---|---|---|---|---|---|---|---|
| ACGCP200343017A | BDL | BDL | BDL | BDL | BDL | BDL | 0.21 | BDL | 0.10 | BDL | 0.32 |
| ACGCP200343018A | BDL | BDL | 0.13 | 0.13 | BDL | 0.37 | 0.29 | BDL | 0.16 | BDL | 1.16 |
| ACGCP200343019A | BDL | BDL | 0.13 | 0.16 | 0.05 | 0.39 | 0.29 | BDL | 0.16 | BDL | 1.27 |
| ACGCP200343020A | BDL | BDL | BDL | BDL | BDL | BDL | 0.27 | BDL | 0.10 | BDL | 0.39 |
| ACGCP200343021A | BDL | BDL | BDL | 0.12 | BDL | 0.36 | 0.31 | BDL | 0.19 | 0.38 | 1.44 |
| ACGCP200343022A | BDL | BDL | 0.13 | 0.15 | 0.04 | 0.39 | 0.28 | BDL | 0.17 | BDL | 1.26 |
| ACGCP200343023A | BDL | BDL | 0.07 | 0.05 | BDL | BDL | BDL | BDL | BDL | BDL | 0.14 |
| ACGCP200343024A | BDL | BDL | BDL | BDL | BDL | 0.35 | 0.29 | 0.08 | 0.22 | BDL | 1.12 |
| ACGCP200343025A | BDL | BDL | 0.12 | 0.19 | 0.09 | 0.37 | 0.24 | BDL | 0.18 | BDL | 1.38 |

Specified impurities are calculated with respect to individual Ref. standards.

TABLE 22 stability of ACGCP200343017A to ACGCP200343025A
ACGCP200343017A to ACGCP200343025A Initial results

| Batch No. | DOA | Time point | pH | BZA | Assay % D-Panthenol | Assay % L-Carnosine | Assay % Lidocaine | Assay % Melatonin | % of degradants (w.r.t Lidocaine) LDRCH |
|---|---|---|---|---|---|---|---|---|---|
| ACGCP200343017A | 2 Apr. 2021 | Initial | NT | 103 | NA | NA | 100 | 98 | 0.02 |
| ACGCP200343018A | 2 Apr. 2021 | Initial | NT | 101 | NA | 103.7 | 98 | 94 | 0.10 |
| ACGCP200343019A | 2 Apr. 2021 | Initial | NT | 103 | 99.8 | 102.2 | 98 | 97 | 0.11 |
| ACGCP200343020A | 2 Apr. 2021 | Initial | NT | NA | NA | NA | 98 | 98 | 0.02 |
| ACGCP200343021A | 2 Apr. 2021 | Initial | NT | NA | NA | 103.1 | 97 | 96 | 0.09 |
| ACGCP200343022A | 2 Apr. 2021 | Initial | NT | NA | 99 | 102.7 | 97 | 98 | 0.11 |
| ACGCP200343023A | 2 Apr. 2021 | Initial | NT | NA | NA | NA | 101 | 99 | 0.05 |
| ACGCP200343024A | 2 Apr. 2021 | Initial | NT | NA | NA | 104.5 | 97 | 100 | 0.23 |
| ACGCP200343025A | 2 Apr. 2021 | Initial | NT | NA | 97 | 104.9 | 97 | 97 | 0.24 |

| Batch No. | MLT RCA | DMA | RRT 0.23 | RRT 0.27 | RRT 0.33 | RRT 0.35 | RRT 0.38 | RRT 0.42 | RRT 0.47 | RRT 0.51 | % Total |
|---|---|---|---|---|---|---|---|---|---|---|---|
| ACGCP200343017A | BDL | BDL | BDL | BDL | BDL | 0.04 | BDL | BDL | 0.02 | BDL | 0.08 |
| ACGCP200343018A | BDL | BDL | 0.02 | BDL | 0.06 | 0.05 | BDL | BDL | 0.03 | BDL | 0.26 |
| ACGCP200343019A | BDL | BDL | 0.02 | 0.03 | 0.01 | 0.06 | 0.05 | BDL | 0.03 | BDL | 0.31 |
| ACGCP200343020A | BDL | BDL | BDL | BDL | BDL | 0.04 | BDL | BDL | 0.02 | BDL | 0.08 |
| ACGCP200343021A | BDL | BDL | 0.02 | BDL | 0.06 | 0.05 | BDL | 0.03 | 0.06 | BDL | 0.31 |
| ACGCP200343022A | BDL | BDL | 0.02 | 0.02 | 0.01 | 0.06 | 0.04 | 0.03 | BDL | BDL | 0.29 |
| ACGCP200343023A | BDL | BDL | BDL | BDL | BDL | 0.02 | BDL | 0.01 | BDL | BDL | 0.08 |
| ACGCP200343024A | BDL | BDL | BDL | BDL | 0.06 | 0.05 | 0.01 | BDL | 0.04 | BDL | 0.39 |
| ACGCP200343025A | BDL | BDL | 0.02 | 0.03 | 0.02 | 0.06 | 0.04 | BDL | 0.03 | BDL | 0.44 |

Specified impurities are calculated with respect to individual Ref. standards.

Batch ACGCP200343001A

Oral rinse formulations without antioxidant were prepared using the compositions as provided in Table 23 below.

TABLE 23

Composition for Lidocaine and Melatonin Oral rinse

| Ingredients | Drug % w/v | Placebo with DGLF % w/v | Placebo without DGLF % w/v |
|---|---|---|---|
| Lidocaine HCl | 2.0% | — | — |
| DGLF | 0.05% | 0.05% | — |
| Melatonin | 0.1% | — | — |
| Kolliphor RH40 | 10.0% | 10.0% | 10.0% |
| Benzyl alcohol | 2.0% | 2.0% | 2.0% |
| Propylene glycol | 10.0% | 10.0% | 10.0% |
| Glycerol | 5.0% | 5.0% | 5.0% |
| Xylitol powder | 7.5% | 7.5% | 7.5% |
| Citric acid monohydrate | 0.69% | 0.69% | 0.69% |
| Tri Sodium citrate dihydrate | 0.53% | 0.53% | 0.53% |
| Sodium hyaluronate | 0.2% | 0.2% | 0.2% |
| PVP K30 | 10.0% | 10.0% | 10.0% |
| Water | Q.s to 100% | Q.s to 100% | Q.s to 100% |

Batch ACGCP200343002A

Oral rinse formulations with antioxidant were prepared using the compositions as provided in Table 24 below.

TABLE 24

Composition for Lidocaine and Melatonin Oral rinse ACGCP200343002A

| Ingredients | Drug % w/v | Placebo with DGLF % w/v | Placebo without DGLF % w/v |
|---|---|---|---|
| Lidocaine HCl | 2.0% | — | — |
| DGLF | 0.05% | 0.05% | — |
| Melatonin | 0.1% | — | — |
| Kolliphor RH40 | 10.0% | 10.0% | 10.0% |
| Benzyl alcohol | 2.0% | 2.0% | 2.0% |
| Propylene glycol | 10.0% | 10.0% | 10.0% |
| Glycerin | 5.0% | 5.0% | 5.0% |
| Xylitol | 7.5% | 7.5% | 7.5% |
| Citric acid monohydrate | 0.69% | 0.69% | 0.69% |
| Sodium citrate | 0.53% | 0.53% | 0.53% |
| Sodium hyaluronate | 0.2% | 0.2% | 0.2% |
| PVP K30 | 10.0% | 10.0% | 10.0% |
| Sodium metabisulphate | 0.02% | 0.02% | 0.02% |
| Water | Q.s to 100% | Q.s to 100% | Q.s to 100% |

TABLE 25

Assay and RS of ACGCP200343001A Lidocaine oral solution

| Batch No. | Formula | DOA | Time point | pH | Assay % Lidocaine | DGLF | Melatonin |
|---|---|---|---|---|---|---|---|
| ACGCP200343001A | without antioxidant | 20 Mar. 2021 | 20 days at RT | NT | 101.9 | 105.1 | 106.4 |
| ACGCP200343002A | with antioxidant | 20 Mar. 2021 | 20 days at RT | NT | 98.2 | 100.3 | 96.4 |

| Batch No. | Sample ID | DOA | Time point | Description | pH |
|---|---|---|---|---|---|
| ACGCP200343001A | (A) with antioxidant | 22 Feb. 2021 | Initial | light yellow colour solution | 3.85 |
|  | (B) without antioxidant | 22 Feb. 2021 | Initial | light yellow colour solution | 3.86 |
|  | without antioxidant | 20 Mar. 2021 | 20 days at RT | light yellow colour solution | NT |
|  |  | 10 Apr. 2021 | 47 days at 40° C. | light yellow colour solution | NT |
|  |  | 10 Apr. 2021 | 47 days at 2-8° C. | light yellow colour solution | NT |

| Batch No. | Assay % Lidocaine | DGLF | Melatonin | % of degradants RRT 1.61 | RRT 2.46 | RRT 2.51 | RRT 3.21 | % Total |
|---|---|---|---|---|---|---|---|---|
| ACGCP200343001A | 98.5 | NT | 100.9 | 0.006 | 0.01 | 0.02 | BDL | 0.04 |
|  | 99.8 | NT | 101.2 | 0.003 | 0.01 | BDL | BDL | 0.01 |
|  | 101.9 | 105.1 | 106.4 | Not done | | | | |
|  | 102.6 | NT | 105.6 | 0.03 | 0.01 | 0.05 | 0.004 | 0.09 |
|  | 106.4 | NT | 108.6 | 0.01 | 0.01 | BDL | BDL | 0.02 |

Batch ACGCP200343003A

Oral rinse formulations were prepared using the compositions as provided in Table 26 below.

TABLE 26

Composition for Lidocaine Oral rinse ACGCP200343003A

| Ingredients | % W/V |
|---|---|
| Lidocaine HCl | 2.0% |
| Kolliphor RH40 | 10.0% |
| Benzyl alcohol | 2.0% |
| Propylene glycol | 10.0% |
| Glycerol | 5.0% |
| Xylitol powder | 7.5% |
| Citric acid monohydrate | 0.1% |
| Sodium hyaluronate | 0.2% |
| PVP K30 | 10.0% |
| Water | Q.s to 100% |

Batch ACGCP200343006A

Oral rinse formulations were prepared using the compositions as provided in Table 27 below.

TABLE 27

Composition for Lidocaine and melatonin Oral rinse

| Ingredients | % W/V |
|---|---|
| Lidocaine HCl | 2.0% |
| Melatonin | 0.1% |
| DGLF | 0.05% |
| Kolliphor RH40 | 10.0% |
| Benzyl alcohol | 2.0% |
| Propylene glycol | 10.0% |
| Glycerol | 5.0% |
| Xylitol powder | 7.5% |
| Citric acid monohydrate | 0.69% |
| Sodium citrate dihydrate | 0.53% |
| Sodium hyaluronate | 0.2% |
| PVP K30 | 10.0% |
| Water | Q.s to 100% |

Batch ACGCP200343007A

Oral rinse formulations were prepared using the compositions as provided in Table 28 below.

TABLE 28

Composition for Lidocaine and melatonin Oral rinse

| Ingredients | % W/V |
|---|---|
| Lidocaine HCl | 2.0% |
| Melatonin | 0.1% |
| DGLF | 0.05% |

TABLE 28-continued

Composition for Lidocaine and melatonin Oral rinse

| Ingredients | % W/V |
|---|---|
| Kolliphor RH40 | 10.0% |
| Benzyl alcohol | 2.0% |
| Propylene glycol | 10.0% |
| Glycerin | 5.0% |
| Xylitol | 7.5% |
| Citric acid monohydrate | 0.69% |
| Sodium citrate | 0.53% |
| Sodium hyaluronate | 0.2% |
| PVP K30 | 10.0% |
| Brilliant Blue | qs |
| Orange flavour | qs |
| Water | Q.s to 100% |

Batch ACGCP200343009A

Oral rinse formulations were prepared using the compositions as provided in Table 29 below.

TABLE 29

Composition for Lidocaine and melatonin Oral rinse

| Ingredients | % W/V |
|---|---|
| Lidocaine HCl | 2.0% |
| Melatonin | 0.1% |
| DGLF | 0.05% |
| Kolliphor RH40 | 10.0% |
| Benzyl alcohol | 2.0% |
| Propylene glycol | 10.0% |
| Glycerol | 5.0% |
| Xylitol powder | 7.5% |
| Citric acid monohydrate | 0.05% |
| Sodium hyaluronate | 0.2% |
| PVP K30 | 10.0% |
| Water | Q.s to 100% |

Batch ACGCP200343010A

Oral rinse formulations were prepared using the compositions as provided in Table 30 below.

TABLE 30

Composition for Lidocaine and melatonin Oral rinse

| Ingredients | % W/V |
|---|---|
| Lidocaine HCl | 2.0% |
| Melatonin | 0.1% |
| DGLF | 0.05% |
| Kolliphor RH40 | 10.0% |
| Benzyl alcohol | 2.0% |
| Propylene glycol | 10.0% |
| Glycerin | 5.0% |
| Xylitol | 7.5% |
| Citric acid monohydrate | 0.05% |
| Sodium hyaluronate | 0.2% |
| PVP K30 | 10.0% |
| Brilliant Blue | qs |
| Orange flavour | qs |
| Water | Q.s to 100% |

Batch ACGCP200343026A

Oral rinse formulations were prepared using the compositions as provided in Table 31 below.

TABLE 31

Composition for Lidocaine and L-Carnosine Oral rinse

| Ingredients | % W/V |
|---|---|
| Lidocaine HCl | 2.0% |
| L-Carnosine | 1.0% |
| Citric acid anhydrous | 0.3318% |
| Tri Sodium citrate dihydrate | 0.9625% |
| Xylitol powder 90 | 7.5% |
| Glycerol | 5.0% |
| Propylene glycol | 10.0% |
| PVP K30 | 10.0% |
| Sodium hyaluronate | 0.2% |
| Water | Qs to 100% |

TABLE 32

Stability data of ACGCP200343026A

| Batch No. | DOA | Time point | pH | BZA | D-Panthenol | L-Carnosine | Lidocaine | Melatonin | % Of degradants (w.r.t Lidocaine) LD RC H |
|---|---|---|---|---|---|---|---|---|---|
| ACGCP200343026A | 4 Apr. 2021 | Initial | NT | NA | NA | 101.3 | 100.5 | NA | ND |

| Batch No. | MLT RC A | DMA | RRT 0.23 | RRT 0.27 | RRT 0.33 | RRT 0.35 | RRT 0.38 | RRT 0.42 | RRT | RRT 0.51 | % Total |
|---|---|---|---|---|---|---|---|---|---|---|---|
| ACGCP200343026A | ND | ND | BDL | BDL | BDL | BDL | BDL | 0.05 | 0.02 | BDL | 0.07 |

Batch ACGCP200343027A

TABLE 33

Composition for Lidocaine and L-Carnosine Oral rinse ACGCP200343027A

| S. No. | Ingredients | % W/V |
|---|---|---|
| 01 | Lidocaine HCl | 2.0% |
| 02 | L-Carnosine | 1.0% |
| 03 | Citric acid anhydrous | 0.3318% |
| 04 | Tri Sodium citrate dihydrate | 0.9625% |
| 05 | Xylitol powder | 7.5% |
| 06 | Glycerol | 5.0% |
| 07 | Propylene glycol | 10.0% |
| 08 | PVP K30 | 10.0% |
| 09 | Sodium hyaluronate | 0.2% |
| 10 | Water | Qs to 100% |

TABLE 34

Stability data of ACGCP200343027A

| Batch No. | Analysis date | Description | Assay % L-Carnosine | Assay % CLX-GEN-G005-C01 | % of impurities RRT 0.67 | % of impurities RRT 1.27 | % of impurities RRT 1.61 | Total |
|---|---|---|---|---|---|---|---|---|
| ACGCP200343027A | Initial 8 May 2021 | clear, off white viscous liquid | 99.2 | 97.8 | 0.02 | 0.05 | 0.17 | 0.24 |

Batch ACGCP200343028A

Oral rinse formulations were prepared using the compositions as provided in Table 36 below.

TABLE 35

Composition for Lidocaine and L-Carnosine Oral rinse

| Ingredients | % W/V |
|---|---|
| Lidocaine HCl | 2.0% |
| L-Carnosine | 1.0% |
| Citric acid anhydrous | 0.1679% |
| Tri Sodium citrate dihydrate | 1.2135% |
| Xylitol powder 90 | 7.5% |
| Glycerol | 5.0% |
| Propylene glycol | 10.0% |
| Methyl paraben | 0.05% |
| Propyl paraben | 0.05% |
| PVP K30 | 10.0% |
| Water | Qs to 100% |

Batch ACGCP200343029A

Oral rinse formulations were prepared using the compositions as provided in Table 36 below.

TABLE 36

Composition for Lidocaine Oral rinse ACGCP200343029A

| Ingredients | % W/V |
|---|---|
| Lidocaine HCl | 2.0% |
| Citric acid anhydrous | 0.1679% |
| Tri Sodium citrate dihydrate | 1.2135% |
| Xylitol powder 90 | 7.5% |
| Glycerol | 5.0% |
| Propylene glycol | 10.0% |
| Methyl paraben | 0.05% |
| Propyl paraben | 0.05% |
| PVP K30 | 10.0% |
| Water | Qs to 100% |

BATCH ACGCP200343030A

Oral rinse formulations were prepared using the compositions as provided in Table 37 below.

TABLE 37

Composition for Lidocaine and D-Panthenol Oral rinse

| Ingredients | % W/V |
|---|---|
| Lidocaine HCl | 2.0% |
| D-Panthenol | 5.0% |
| Citric acid anhydrous | 0.1679% |
| Tri Sodium citrate dihydrate | 1.2135% |
| Xylitol powder 90 | 7.5% |
| Glycerol | 5.0% |
| Propylene glycol | 10.0% |
| Methyl paraben | 0.05% |
| Propyl paraben | 0.05% |
| PVP K30 | 10.0% |
| Water | Qs to 100% |

BATCH ACGCP200343031A

Oral rinse formulations were prepared using the compositions as provided in Table 38 below.

TABLE 38

Composition for Lidocaine and L-Carnosine Oral rinse

| Ingredients | % W/V |
|---|---|
| Lidocaine HCl | 2.0% |
| L-Carnosine | 1.0% |
| Citric acid anhydrous | 0.1679% |
| Tri Sodium citrate dihydrate | 1.2135% |
| Xylitol powder 90 | 7.5% |
| Glycerol | 5.0% |
| Propylene glycol | 10.0% |
| PVP K30 | 10.0% |
| Water | Qs to 100% |

TABLE 39

Stability data
ACGCP200343 Oral Solution

| | | | | | | % Degradants | | | | | | |
|---|---|---|---|---|---|---|---|---|---|---|---|---|
| | | | | | | Method I | | | Method II | | | |
| | | | | | | H. Individual | H. Individual | | Specified | | Unknown | |
| | Sample | | Assay % | | | Unknown | Unknown | % | Lidocaine | 2,6- | Highest | % |
| Batch No. | ID | Condition | LD | DXP | LC | Carnosine | DXP | Total | RC H | DMA | Individual | Total |
| In House Specifications/Limits, % | | | 95-105 | 95-105 | 95-105 | 1.0 | 1.0 | 3.0 | 0.5 | 0.5 | 0.5 | 1.50 |
| ACGCP200343034A | LD, LC, DXP | Initial | 103.6 | 107.1 | 104.3 | 0.24 | 0.14 | 0.73 | BDL | ** | 0.038 | 0.038 |
| ACGCP200343035A | LD, LC, DXP | Initial | 103.1 | 105.8 | 102.9 | 0.16 | 0.14 | 0.99 | BDL | ** | 0.026 | 0.026 |

NOTE:
LD—Lidocaine:
LC—L-Carnosine;
DXP—Dexpanthenol;
NA—Not applicable,
H.I—Highest Individual
Method I (IH) for L-Carnosine & DXP Assay & Related Substances.
Method II (USP) for Lidocaine Hydrochloride Assay & Related Substances.
** Impurity not identified/quantified due to lack of Reference standard.

TABLE 40

Stability data

| | | % Of degradants | | | | |
|---|---|---|---|---|---|---|
| Batch No. | Conditions | MLT · RC A | 0.07 | 0.17 | 0.24 | Total |
| ACGCP200343029A | Initial | ND | ND | ND | 0.01 | 0.01 |
| ACGCP200343030A | Initial | ND | 0.03 | ND | 0.01 | 0.04 |
| ACGCP200343031A | Initial | ND | 0.02 | ND | 0.01 | 0.03 |
| ACGCP200343032A | Initial | ND | 0.04 | 0.05 | 0.01 | 0.10 |

TABLE 41

Stability Data

| | | Assay % | | | |
|---|---|---|---|---|---|
| Batch No. | Condition | Melatonin | Lidocaine | D-Panthenol | L-Carnosine |
| ACGCP200343029A | Initial | NA | 98.8 | NA | NA |
| ACGCP200343030A | Initial | NA | NA | 104.3 | NA |
| ACGCP200343031A | Initial | NA | NA | NA | 96.6 |
| ACGCP200343032A | Initial | NA | 98.3 | 103 | 97.2 |

TABLE 42

Stability Data
Repeat Analysis Results

| Batch No. | Condition | Lidocaine | D-Panthenol | L-Carnosine |
|---|---|---|---|---|
| ACGCP200343014A | 40° C.-1M | 99.1 | 95.7 | 93.9 |
| ACGCP200343031A | Initial | 97.2 | NA | 96.2 |
| ACGCP200343032A | Initial | 98.1 | 103.2 | 97.1 |

TABLE 43

Stability Data
Objective: Topreparedrug solutions by dissolving
individuallyLidocaine HCl, L-Carnosine & D-Panthenol
using 0.05M citrate buffer with pH 4.0, pH 5.0 & pH 6.0 as vehicle.
ACGCP200343033A

| S. No. | Ingredients | % W/V | % W/V | % W/V |
|---|---|---|---|---|
| 01 | Lidocaine HCl | 2.0% | — | — |
| 02 | L-Carnosine | — | — | 1.0% |
| 03 | D-Panthenol | — | 5.0% | — |
| 04 | Citric acid anhydrous | Qs to pH 4.0 Qs to pH 5.0 Qs to pH 6.0 | Qs to pH 4.0 Qs to pH 5.0 Qs to pH 6.0 | Qs to pH 4.0 Qs to pH 5.0 Qs to pH 6.0 |
| 05 | Tri Sodium citrate dihydrate | Qs to pH 6.0 | Qs to pH 6.0 | Qs to pH 6.0 |
| 06 | Water | Qs to 100% | Qs to 100% | Qs to 100% |

Observations: All solutions were clear.
Solutions were kept at 40° C. in hot air oven(FRD) & 25° C. for the future stability checking

TABLE 44

Stability Data
Objective: Topreparedrug solutions by
dissolving individuallyLidocaine HCl, L-Carnosine
& D-Panthenol in Water.
ACGCP200343033A

| S. No. | Ingredients | % W/V | % W/V | % W/V |
|---|---|---|---|---|
| 01 | Lidocaine HCl | 2.0% | — | — |
| 02 | L-Carnosine | — | — | 1.0% |
| 03 | D-Panthenol | — | 5.0% | — |
| 04 | Water | Qs to 100% | Qs to 100% | Qs to 100% |

Observations: All solutions were clear.
Solutions were kept at 40° C. in hot air oven(FRD) & 25° C. for the future stability checking Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

What is claimed is:

1. A composition comprising: lidocaine, or a salt or a hydrate or a solvate thereof, L-Carnosine, or a salt or a hydrate or a solvate thereof; and dexpanthenol; or a salt or a hydrate or a solvate thereof, wherein said composition is formulated as an oral formulation; and wherein the composition further comprises at least one excipient that is a fatty acid derivative selected from a group consisting of diglyceryl lauryl fumarate, diglyceryl lauryl succinate, diglyceryl capryl succinate, and any combination thereof.

2. The composition of claim 1, wherein the composition comprises lidocaine, or a salt or a hydrate or a solvate thereof; L-Carnosine, or a salt or a hydrate or a solvate thereof; and dexpanthenol; or a salt or a hydrate or a solvate thereof; in a weight ratio ranging from 1:1:1 to 7:1:20.

3. The composition of claim 1, wherein the composition comprises, or a salt or a hydrate or a solvate thereof, L-Carnosine, or a salt or a hydrate or a solvate thereof; and dexpanthenol; or a salt or a hydrate or a solvate thereof, in a weight ratio ranging from 1:1:1 to 5:1:10.

4. The composition of claim 1, wherein the composition further comprises at least one additional excipient.

5. The composition of claim 1, wherein the composition further comprises at least one other active agent.

6. The composition as claimed in claim 4, wherein the at least one additional excipient is selected from a group consisting of a diluent, an antioxidant, a preservative, a solvent, a flavoring agent, a sweetener, a fatty acid or derivative thereof, an amino acid or metabolite or derivative thereof, a vitamin, a surfactant, a solubilizer, a stabilizer, and any combination thereof.

7. The composition as claimed in claim 5, wherein the at least one other active agent is selected from a group consisting of benzocaine, clonidine, bupivacaine, ropivacaine, mepivacaine, morphine, fentanyl, orthoform, levo-bupivacaine, bibucaine, prilocaine, acetaminophen, procaine, diphenhydramine, polaprezinc, benzydamine, pentoxifylline, ortetracaine, ketamine, misoprostol, amifostine, palifermin, chlorhexidine gluconate, dusquetide, melatonin, indraline, androstenetriol, actovegin, rebamipide, EC-18, brilacidin, validive, streptomycin, kanamycin, neomycin, gentamicin, betamethasone, betamethasone esters, clobetasol, clobetasol propionate, clobetasone, clocortolone, clocortolone esters, dexamethasone, dexamethasone esters, diflorasone, diflucortolone, diflucortolone valerate, fluclorolone, flumetasone, fluocortin, fluocortolone, fluocortolone esters, fluprednidene acetate, fluticasone, fluticasone furoate, fluticasone propionate, halometasone, meprednisone, mometasone, mometasone furoate, ulobetasol, 2-mercaptoethane sodium sulphonate, 2-Mercaptoethylguanidine, methylprednisolone, beclomethasone dipropionate, fluocinonide, betamethasone sodium phosphate, prednisolone, colchicine, azathioprine, thalidomide, dapsone, mycophenolate mofetil, adalimumab, clofazimine, levamisole, hydrocortisone sodium succinate, montelukast, triamcinolone, sulodexide, α-Lipoic acid, cysteamine, folic acid, hydrolytic enzyme, mucotrol, traumeel, tretinoin, calcipotriene, calcitriol, ergosterol, 1α-hydroxycholecalciferol, vitamin D2, vitamin D3, ascorbic acid, calcium ascorbate, nicotinamide ascorbate, sodium ascorbate, α-carotene, β-carotene, δ-carotene, vitamin A, cobamamide, hydroxocobalamin, sodium folate, vitamin B12, menadiol, menadione, menadoxime, menaquinones, phylloquinone, vitamin K5, inositol, α-tocopherol, γ-tocopherol, vitamin E, zinc, selenium, potassium, copper, manganese, aluminum, zinc sulfate, magnesium, magnesium aluminum hydroxide, magnesium sulfate, calcium phosphate, magnesium stearate, magnesium silicate, magnesium chloride, magnesium bromide, magnesium acetate, magnesium lactate, magnesium pidolate, magnesium thiosulphate, Cu2+ salts, copper sulfate pentahydrate, copper sulfate, copper malonate, copper citrate, copper oxalate, copper tartarate, copper lactate, copper chloride, copper bromide, copper pidolate, copper phosphate, copper nitrate, copper thiosulphate, Al+3 salts, aluminum oxide, aluminum palmitate, aluminum stearate, aluminum chloride, aluminum oxychloride, aluminum barium silicate, Aluminum magnesium hydroxide stearate, aluminum propionate aluminum dipropionate, aluminum aceto propionate, aluminum citro propionate, aluminum lacto propionate, aluminum tartaro propionate, aluminum acetodipropionate, aluminum citrodipropionate, aluminum lacto dipropionate, aluminum tartarodipropionate, polymers, carbomer, methyl cellulose, sodium carboxyl methyl cellulose, carrageenan, colloidal silicon dioxide, hydroxypropyl cellulose, hydroxypropyl methyl cellulose, polyethylene oxide, hyaluroinic acid, hydrated silica, hydroxypropyl chitosan, chitosan sulfate, ethyl cellulose, hydroxymethyl cellulose, carboxy methyl cellulose, chitosan pyrrolidone carboxylate, amphotericin B, benzoxonium chloride, chlorhexidine, chlortetracycline, clotrimazole, cetylpyridinium chloride, domiphen bromide, amoxicillin, cephalexin, ciprofloxacin, clindamycin, azithromycin, sulfamethoxazole, trimethoprim, clavulanate, levofloxacin, doxycycline, eugenol, hexetidine, hydrogen peroxide, mepartricin, metronidazole, miconazole, minocycline, natamycin, oxyquinoline, polynoxylin, sodium perborate, tetracycline, tibezonium iodide, amlexanox, acetylsalicylic acid, becaplermin, epinephrine, adrenalone, triclosan, mycophenolic acid, cyclosporines, leflunomide, teriflunomide, ciclosporin, pimecrolimus, tacrolimus, voclosporin, lenalidomide, pomalidomide, sirolimus, everolimus, ridaforolimus, temsirolimus, umirolimus, zotarolimus, baricitinib, blisibimod, nilotinib, filgotinib, tofacitinib, upadacitinib, abatacept, belatacept, etanercept, pegsunercept, aflibercept, alefacept, rilonacept, glyceryl trinitrate, isosorbide dinitrate, isosorbide mononitrate, isoamyl nitrite, apremilast, arofylline, atizoram, benafentrine, catramilast, CC-1088, CDP-840, CGH-2466, cilomilast, cipamfylline, crisaborole, denbutylline, difamilast, drotaverine, etazolate, filaminast, glaucine, HT-0712, ICI-63197 indimilast, irsogladine, lavamilast, lirimilast, lotamilast, luteolin, mesembrenone, mesembrine, mesopram, oglemilast, piclamilast, pumafentrine, revamilast Ro 20-1724, roflumilast, rolipram, ronomilast, RPL-554, RS-25344, tetomilast, tofimilast, YM-976, zardaverine, ibudilast, roflumilas, adibendan, amrinone, anagrelide, bucladesine, carbazeran, cilostamide, cilostazol, enoximone, imazodan, KMUP-1, meribendan, milrinone, olprinone, parogrelil, pimobendan, quazinone, siguazodan, trequinsin, vesnarinone, pde 5 inhibitors, acetildenafil, aildenafil, avanafil, beminafil, benzamidenafil, dasantafil, icariin, gisadenafil, homosildenafil, lodenafil, mirodenafil, MY-5445, nitrosoprodenafil, norcarbodenafil, SCH-51866, sildenafil, sulfoaildenafil, T-0156, tadalafil, udenafil, vardenafil, abrocitinib, momelotinib, oclacitinib, peficitinib, ruxolitinib, tasocitinib, CP-690550, atiprimod, AZD-1480, CHZ868, cucurbitacin I, CYT387, lestaurtinib, NSC-7908, NSC-33994, pacritinib, SD-1008, cercosporamide, decernotinib, TCS-21311, WHI-P 15 ZM-39923, ZM-449829, methotrexate, diclofenac, indomethacin, sulindac, mefenamic acid, piroxicam, ibuprofen, ketoprofen, naproxen, phenylbutazone, meloxicam, nimesulide, celecoxib, etoricoxib WBI-1001, MRX-6, valdecoxib, and any mixture thereof.

8. The composition of claim 1, wherein the composition is formulated as an oral rinse formulation.

9. The composition of claim 1, wherein the composition comprises
lidocaine or a salt or a hydrate or a solvate thereof in an amount ranging from 0.25% w/v to 10% w/v;
L-Carnosine or a salt or a hydrate or a solvate thereof in an amount ranging from 0.25% w/v to 5% w/v;
dexpanthenol or a salt or a hydrate or a solvate thereof in an amount ranging from 0.5% w/v to 25% w/v;
a polyhydric alcohol in an amount ranging from 5% w/v to 30% w/v;
an anti-oxidant in an amount ranging from 0.01% w/v to 3% w/v;
a buffer in an amount ranging from 0.02% w/v to 5% w/v;
a surfactant in an amount ranging from 1% w/v to 30% w/v;
a sweetener in an amount ranging from 0.5% w/v to 25% w/v;
a preservative in an amount ranging from 0.01% w/v to 5% w/v; and
water in an amount ranging from 35% w/v to 90% w/v.

10. The composition of claim 9, wherein the polyhydric alcohol is selected from the group consisting of polyhydric alkanes, polyhydric alkane esters, polyalkene glycols, and mixtures thereof.

11. The composition of claim 9, wherein the antioxidant is selected from the group consisting of sodium metabisulfite, vitamin A, tocopherol, ascorbic acid or salt or derivative thereof, tartaric acid or salt or derivative thereof, retinyl palmitate, sesamol, thiol derivatives, butylated hydroxy anisole (BHA), butylated hydroxyl toluene (BHT), and mixtures thereof.

12. The composition of claim 9, wherein the buffer is selected from the group consisting of citric acid or salt or derivative thereof, benzoic acid or salt or derivative thereof, sorbic acid or salt or derivative thereof, succinic acid or salt or derivative thereof, and mixtures thereof.

13. The composition as claimed in claim 9, wherein the sweetener is selected from the group consisting of sorbitol, xylitol, mannitol, maltitol, inositol, allitol, altriol, dulcitol, galactitol, glucitol, hexitol, iditol, pentitol, ribitol, erythritol, and mixtures thereof.

14. The composition of claim 8, wherein the composition further comprises hyaluronic acid, or a salt or derivative thereof, in an amount ranging from 0.02% w/v to 15% w/v.

15. The composition as of 8, wherein the composition has a pH ranging from 4.5 to 7.5.

16. A method of treating oral, pharyngeal, oropharyngeal and esophageal conditions in a patient in need thereof comprising administering to a subject a therapeutically effective amount of the composition of claim 1.

* * * * *